United States Patent [19]

Short

[11] Patent Number: 5,589,392
[45] Date of Patent: Dec. 31, 1996

[54] NUCLEIC ACID CONSTRUCT ENCODING A NUCLEAR TRANSPORT PEPTIDE OPERATIVELY LINKED TO AN INDUCIBLE PROMOTER

[75] Inventor: Jay M. Short, Encinitas, Calif.

[73] Assignee: Stratagene, La Jolla, Calif.

[21] Appl. No.: 158,718

[22] Filed: Nov. 29, 1993

Related U.S. Application Data

[63] Continuation of Ser. No. 640,983, Jan. 14, 1991, abandoned.

[51] Int. Cl.$^6$ .......................... C12N 15/09; C12N 15/63; C07H 21/02; C07H 21/04
[52] U.S. Cl. ................... 435/320.1; 536/23.1; 536/23.4; 536/23.7; 536/24.1
[58] Field of Search ............................ 536/24.1, 23.1; 800/2

[56] References Cited

PUBLICATIONS

Lyons et al., Mol. and Cell. Biol., 7:2451–2456 (1987)—Pentapeptide Nuclear Localization Signal in Adenovirus E1a.

Scangas et al (1987) Adv. Genet. 24, 285–322.
Hu et al (1987) Cell 48, 555–566.
Dunn et al (1988) Gene 68, 259–266.
Langford et al (1986) Cell 46, 575–582.
Miller et al (1980) The Operon, 134.
Hu et al (1987) Cell 48, 555–566.
Sadowski et al (1988) Nature, 335, 563–54.
Scangos et al (1987) Adv in Genet. 27, 285–322.

Primary Examiner—Jacqueline M. Stone
Assistant Examiner—Deborah Crouch
Attorney, Agent, or Firm—Albert P. Halluin, Esq.; Pennie & Edmonds

[57] ABSTRACT

A system for regulating expression of eukaryotic genes in cells is described. The system contains two recombinant DNA molecules, a first molecule that encodes a nucleus-targeted inducible repressor polypeptide, and a second molecule that encodes an operator-regulated reporter polypeptide. Transgenic animals containing the system, and methods for using the system are also described.

2 Claims, 15 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
            ( A ) LENGTH: 7 amino acids
            ( B ) TYPE: amino acid
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Pro   Lys   Lys   Lys   Arg   Lys   Val
                                   5

( 2 ) INFORMATION FOR SEQ ID NO:2:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:2:

Lys   Arg   Pro   Arg   Pro
 1                                5

( 2 ) INFORMATION FOR SEQ ID NO:3:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TGTGGAATTG TGAGCGCTCA CAATTCCACA                                                                    30

( 2 ) INFORMATION FOR SEQ ID NO:4:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:41

ATTGTGAGCG CTCACAAT                                                                                 18

( 2 ) INFORMATION FOR SEQ ID NO:5:

( i ) SEQUENCE CHARACTERISTICS:
            ( A ) LENGTH: 7224 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI- SENSE: NO ( x i ) SEQUENCE DESCRIPTION: SEQ ID NO:5:

TCGCGCGTTT CGGTGATGAC GGTGAAAACC TCTGACACAT GCAGCTCCCG GAGACGGTCA    60
CAGCTTGTCT GTAAGCGGAT GCCGGGAGCA GACAAGCCCG TCAGGGCGCG TCAGCGGGTG    120
TTGGCGGGTG TCGGGGCTGG CTTAACTATG CGGCATCAGA GCAGATTGTA CTGAGAGTGC    180
ACCACGAACA AAGGACCCAA CACGGGTGGG TTTTATTCTG TCTTTTTATT GCGGATCCCC    240
TCAGAAGAAC TCGTCAAGAA GGCGATAGAA GGCGATGCGC TGCGAATCGG GAGCGGCGAT    300
ACCGTAAAGC ACCAGGAAGC GGTCAGCCCA TTCGCCGCCA AGCTCTTCAG CAATATCACG    360
GGTAGCCAAC GCTATGTCCT GATAGCGGTC CGCCACACCC ACCCGGCCAC AGTCGATGAA    420
TCCAGAAAAG CGGCCATTTT CCACCATGAT ATTCGGCAAG CAGGCATCGC CATGGGTCAC    480
GAGGAGATCC TCGCCGTCGG GCATGCGCGC CTTGAGCCTG GCAACAGTT CGGCTGGCGC     540
GAGCCCCTGA TGCTCTTCGT CCAGATCATC CTGATCGACA AGACCCGCTT CCATCCGAGT    600
ACGTGCTCGC TCGATGCGAT GTTTCGCTTG GTGGTCGAAT GGGCAGGTAG CCGGATCAAG    660
CGTATGCAGC CGCCGCATTG CATCAGCCAT GATGGATACT TTCTCGGCAG GAGCAAGGTG    720
AGATGACAGG AGATCCTGCC CCGGCACTTC GCCCAATAGC AGCCAGTCCC TTCCCGCTTC    780
AGTGACAACG TCGAGCACAG CTGCGCAAGG AACGCCCGTC GTGGCCAGCC ACGATAGCCG    840
CGCTGCCTCG TCCTGCAGTT CATTCAGGGC ACCGGACAGG TCGGTCTTGA CAAAAGAAC    900
CGGGCGCCCC TGCGCTGACA GCCGGAACAC GGCGGCATCA GAGCAGCCGA TTGTCTGTTG    960
TGCCCAGTCA TAGCCGAATA GCCTCTCCAC CCAAGCGGCC GGAGAACCTC CGTGCAATCC    1020
ATCTTGTTCA ATGGCCGATC CCATATTGGC TGCAGGGTCG CTCGGTGTTC CAGGCCACAC    1080
GCGTCACCTT AATATGCGAA GTGGACCTGG GACCGCGCCG CCCCGACTGC ATCTCCGTGT    1140
TCGAATTCGC CAATGACAAG ACGCTGGGCG GGGTTGCTC GACATTGGGT GGAAACATTC     1200
CAGGCCTGGG TGGAGAGGCT TTTTGCTTCC TCTTGCAAAA CCACACTGCT CGACATTGGG    1260

| | | | | | |
|---|---|---|---|---|---|
| TGGAAACATT | CCAGGCCTGG | GTGGAGAGGC | TTTTTGCTTC | CTCTTGCAAA | ACCACACTGC | 1320 |
| TCGATATGCG | GTGTGAAATA | CCGCACAGAT | GCGTAAGGAG | AAAATACCGC | ATCAGGAAAT | 1380 |
| TGTAAACGTT | AATATTTTGT | TAAAATTCGC | GTTAAATTTT | TGTTAAATCA | GCTCATTTTT | 1440 |
| TAACCAATAG | GCCGAAATCG | GCAAAATCCC | TTATAAATCA | AAGAATAGA | CCGAGATAGG | 1500 |
| GTTGAGTGTT | GTTCCAGTTT | GGAACAAGAG | TCCACTATTA | AGAACGTGG | ACTCCAACGT | 1560 |
| CAAAGGGCGA | AAAACCGTCT | ATCAGGGCGA | TGGCCCACTA | CGTGAACCAT | CACCCTAATC | 1620 |
| AAGTTTTTTG | GGGTCGAGGT | GCCGTAAAGC | ACTAAATCGG | AACCCTAAAG | GGAGCCCCG | 1680 |
| ATTTAGAGCT | TGACGGGGAA | AGCCGGCGAA | CGTGGCGAGA | AAGGAAGGGA | AGAAAGCGAA | 1740 |
| AGGAGCGGGC | GCTAGGGCGC | TGGCAAGTGT | AGCGGTCACG | CTGCGCGTAA | CCACCACACC | 1800 |
| CGCCGCGCTT | AATGCGCCGC | TACAGGGCGC | GTCGCGCCAT | TCGCCATTCA | GGCTACGCAA | 1860 |
| CTGTTGGCAA | GGGCGATCGG | TGCGGGCCTC | TTCGCTATTA | CGCCAGCTGG | CGAAGGGGGG | 1920 |
| ATGTGCTGCA | AGGCGATTAA | GTTGGGTAAC | GCCAGGGTTT | TCCCAGTCAC | GACGTTGTAA | 1980 |
| AACGACGCCC | AGTGAATTGT | AATACGACTC | ACTATAGGGC | GAATTGGAGC | TAGGCCTACG | 2040 |
| TAGCGCGCGA | GCTCCACCGC | GGTGGCAGTA | CAATCTGCTC | TGATGCCGCA | TAGTTAACCC | 2100 |
| AGTATCTGCT | CCCTGCTTGT | GTGTTGGAGG | TCGCTGAGTA | GTGCGCGAGC | AAAATTTAAG | 2160 |
| CTACAACAAG | GCAAGGCTTG | ACCGACAATT | GCATGAAGAA | TCTGCTTAGG | GTTAGGCGTT | 2220 |
| TTGCGCTGCT | TCGCGATGTA | CGGGCCAGAT | ATACGCGTAT | CTGAGGGGAC | TAGGGTGTGT | 2280 |
| TTAGGCGAAA | AGCGGGGCTT | CGGTTGTACG | CGGTTAGGAG | TCCCCTCAGG | ATATAGTAGT | 2340 |
| TTCGCTTTTG | CATAGGGAGG | GGGAAATGTA | GTCTTATGCA | ATACACTTGT | AGTCTTGCAA | 2400 |
| CATGGTAACG | ATGAGTTAGC | AACATGCCTT | ACAAGGAGAG | AAAAAGCACC | GTGCATGCCG | 2460 |
| ATTGGTGGAA | GTAAGGTGGT | ACGATCGTGC | CTTATTAGGA | AGGCAACAGA | CAGGTCTGAC | 2520 |
| ATGGATTGGA | CGAACCACTG | AATTCCGCAT | TGCAGAGATA | ATTGTATTTA | AGTGCCTAGC | 2580 |
| TCGATACAAT | AAACGCCATT | TGACCATTCA | CCACATTGGT | GTGCACCTTC | AAGCTTGGAC | 2640 |
| AAACTACCTA | CAGAGATTTA | AAGCTCTAAG | GTAAATATAA | AATTTTTAAG | TGTATAATGT | 2700 |
| GTTAAACTAC | GGATCCGTCT | CCCATTAGGC | CTACAATGGT | GAGACAAGTA | GCCAACAGGG | 2760 |
| AAGGGTTGCA | AATATCATTT | GGGCACACCT | ATGATAATAT | TGATGAAGCA | GACAGTATTC | 2820 |
| AGCAAGTAAC | TGAGAGGTGG | GAAGCTCAAA | GCCAAGTCC | TAATGTGCAG | TCAGGTGAAT | 2880 |
| TTATTGAAAA | ATTTGAGGCT | CCTGGTGGTG | CAAATCAAAG | AACTGCTCCT | CAGGGATCCT | 2940 |
| AATTGTTTGT | GTATTTTAGA | TTCCAACCAA | GCTTGGAATT | CCTTTGTGTT | ACATTCTTGA | 3000 |
| ATGTCGCTCG | CAGTGACATT | AGCATTCCGG | TACTGTTGGT | AAAATGGAAG | ACGCCAAAAA | 3060 |
| CATAAAGAAA | GGCCCGGCGC | CATTCTATCC | TCTAGAGGAT | GGAACCGCTG | GAGAGCAACT | 3120 |
| GCATAAGGCT | ATCAAGAGAT | ACGCCCTGGT | TCCTGGAACA | ATTGCTTTTA | CAGATGCACA | 3180 |
| TATCGAGGTG | AACATCACGT | ACGCGGAATA | CTTCGAAATG | TCCGTTCGGT | TGGCAGAAGC | 3240 |
| TATGAAACGA | TATGGGCTGA | ATACAAATCA | CAGAATCGTC | GTATGCAGTG | AAAACTCTCT | 3300 |
| TCAATTCTTT | ATGCCGGTGT | TGGGCGCGTT | ATTTATCGGA | GTTGGAGTTG | CGGGGGGGAA | 3360 |
| CGACATTTAT | AATGAACGTG | AATTGCTCAA | CAGTATGAAC | ATTTCGCAGC | CTACCGTAGT | 3420 |
| GTTTGTTTCC | AAAAAGGGGT | TGCAAAAAAT | TTTGAACGTG | CAAAAAAAAT | TACCAATAAT | 3480 |
| CCAGAAAATT | ATTATCATGG | ATTCTAAAAC | GGATTACCAG | GGATTTCAGT | CGATGTACAC | 3540 |
| GTTCGTCACA | TCTCATCTAC | CTCCCGGTTT | TAATGAATAC | GATTTTGTAC | CAGAGTCCTT | 3600 |
| TGATCGTGAC | AAAACAATTG | CACTGATAAT | GAATTCCTCT | GGATCTACTG | GGTTACCTAA | 3660 |

```
GGGTGTGGCC CTTCCGCATA GAACTGCCTG CGTCAGATTC TCGCATGCCA GAGATCCTAT    3720
TTTTGGCAAT CAAATCATTC CGGATACTGC GATTTTAACT GTTGTTCCAT TCCATCACGG    3780
TTTTGGAATG TTTACTACAC TCGGATATTT GATATGTGGA TTTCGAGTCG TCTTAATGTA    3840
TAGATTTGAA GAAGAGCTGT TTTTACGATC CCTTCAGGAT TACAAAATTC AAAGTGCGTT    3900
GCTAGTACCA ACCCTATTTT CATTCTTCGC CAAAAGCACT CTGATTGACA AATACGATTT    3960
ATCTAATTTA CACGAAATTG CTTCTGGGGG CGCACCTCTT TCGAAAGAAG TCGGGGAAGC    4020
GGTTGCAAAA CGCTTCCATC TTCCAGGGAT ACGACAAGGA TATGGCCTCA CTGAGACTAC    4080
ATCAGCTATT CTGATTACAC CCGAGGGGGA TGATAAACCG GGCGCGGTCG GTAAAGTTGT    4140
TCCATTTTTT GAAGCGAAGG TTGTGGATCT GGATACCGCG AAAACGCTGG GCGTTAATCA    4200
CAGAGGCGAA TTATGTGTCA GAGGACCTAT GATTATGTCC GGTTATGTAA CAATCCGGA    4260
AGCGACCAAC GCCTTGATTG ACAAGGATGG ATGGCTACAT TCTGGAGACA TAGCTTACTG    4320
GGACGAAGAC GAACACTTCT TCATAGTTGA CCGCTTGAAG TCTTTAATTA AATACAAAGG    4380
ATATCAGGTG GCCCCCGCTG AATTGGAATC GATATTGTTA CAACACCCCA ACATCTTCGA    4440
CGCGGGCGTG GCAGGTCTTC CCGACGATGA CGCCGGTGAA CTTCCGCCG CCGTTGTTGT    4500
TTTGGAGCAC GGAAAGACGA TGACGGAAAA AGAGATCGTG GATTACGTCG CCAGTCAAGT    4560
AACAACCGCG AAAAAGTTGC GCGGAGGAGT TGTGTTTGTG GACGAAGTAC CGAAAGGTCT    4620
TACCGGAAAA CTCGACGCAA CAAAAATCAG AGAGATCCTC ATAAAGGCCA GAAGGGCGG    4680
AAAGTCCAAA TTGTAAAATG TAACTCTATT CAGCGATGAC GAAATTCTTA GCTATTGTAA    4740
TATTATATGC AAATTGATGA ATGGTAATTT TGTAATTGTG GGTCACTGTA CTATTTTAAC    4800
GAATAATAAA ATCAGGTATA GGATGGGGGA GGCTAACTGA AACACGGAAG GAGACAATAC    4860
CGGAAGGAAC CCGCGCTAIG ACGGCAATAA  AAAGACAGM TAAAACGRAG GGGTGTTGGG    4920
TCGTTTGTTC ATAAACGCGG GGTTCGGTCC CAGGGCTGGC ACTCTGTCGA TACCCCACCG    4980
AGACCCCATT GGGGCCAATA CGCCCGCGTT TCTTCCTTTT CCCCACCCCA CCCCCCAAGT    5040
TCGGGTGAAG GCCCAGGGCT CGCAGCCAAC GTCGGGGCGG CAGGCCCTGC CATAGCCACT    5100
GGCCCCGTGG GTTAGGGACG GGGTCCCCCA TGGGGAATGG TTTATGGTTC GTCCGGGCTA    5160
GCCGGCAGCT GCATTAATGA ATCGGCCAAC GCGCGGGGAG ACCCGGTTTG CGTATTGGGC    5220
GCTCTTCCGC TTCCTCGCTC ACTGACTCGC TGCGCTCGGT CGTTCGGCTG CGGCGAGCGG    5280
TATCAGCTCA CTCAAGGCG GTAATACGGT TATCCACAGA ATCAGGGGAT AACGCAGGAA    5340
AGAACATGTG AGCAAAAGGC CAGCAAAAGG CCAGGAACCG TAAAAAGGCC GCGTTGCTGG    5400
CGTTTTTCCA TAGGCTCCGC CCCCCTGACG AGCATCACAA AAATCGACGC TCAAGTCAGA    5460
GGTGGCGAAA CCCGACAGGA CTATAAAGAT ACCAGGCGTT TCCCCCTGGA AGCTCCCTCG    5520
TGCGCTCTCC TGTTCCGACC CTGCCGCTTA CCGGATACCT GTCCGCCTTT CTCCCTTCGG    5580
GAAGCGTGGC GCTTTCTCAA TGCTCACGCT GTAGGTATCT CAGTTCGGTG TAGGTCGTTC    5640
GCTCCAAGCT GGGCTGTGTG CACGAACCCC CCGTTCAGCC CGACCGCTGC GCCTTATCCG    5700
GTAACTATCG TCTTGAGTCC AACCCGGTAA GACACGACTT ATCGCCACTG GCAGCAGCCA    5760
CTGGTAACAG GATTAGCAGA GCGAGGTATG TAGGCGGTGC TACAGAGTTC TTGAAGTGGT    5820
GGCCTAACTA CGGCTACACT AGAAGGACAG TATTTGGTAT CTGCGCTCTG CTGAAGCCAG    5880
TTACCTTCGG AAAAAGAGTT GGTAGCTCTT GATCCGGCAA ACAAACCACC GCTGGTAGCG    5940
GTGGTTTTTT TGTTTGCAAC GAGCAGATTA CGCGCAGAAA AAAGGATCT CAAGAAGATC    6000
CTTTGATCTT TTCTACGGGG TCTGACGCTC AGTGGAACGA AAACTCACGT TAAGGGATTT    6060
```

-continued

| | | | | | | |
|---|---|---|---|---|---|---|
| TGGTCATGAG | ATTATCAAAA | AGGATCTTCA | CCTAGATCCT | TTTAAATTAA | AAATGAAGTT | 6120 |
| TTAAATCAAT | CTAAAGTATA | TATGAGTAAA | CTTGGTCTGA | CAGTTACCAA | TGCTTAATCA | 6180 |
| GTGAGGCACC | TATCTCAGCG | ATCTGTCTAT | TTCGTTCATC | CATAGTTGCC | TGACTCCCCG | 6240 |
| TCGTGTAGAT | AACTACCATA | CGGGAGGGCT | TACCATCTGG | CCCCAGTGCT | GCAATGATAC | 6300 |
| CGCGAGACCC | ACGCTCACCG | GCTCCAGATT | TATCAGCAAT | AAACCAGCCA | GCCGGAAGGG | 6360 |
| CCGAGCGCAG | AAGTGGTCCT | GCAACTTTAT | CCGCCTCCAT | CCAGTCTATT | AATTGTTGCC | 6420 |
| GGGAAGCTAG | AGTAAGTAGT | TGGGGAGTTA | ATAGTTTGRG | CAAGGTTGTT | GCCATTGCTA | 6480 |
| CAGGCATCGT | GGTGTCACGC | TCGTCGTTTG | GTATGGCTTC | ATTCAGCTCC | GGTTCCCAAC | 6540 |
| GATCAAGGCG | AGTTACATGA | TCCCCCATGT | TGTGCAAAAA | AGCGGTTAGC | TCCTTCGGTC | 6600 |
| CTCCGATCGT | TGTCAGAAGT | AAGTTGGCCG | CAGTGTTATC | ACTCATGGTT | ATGGCAGCAC | 6660 |
| TGCATAATTC | TCTTACTGTC | ATGCCATCCG | TAAGATGCTT | TTCTGTGACT | GGTGAGTACT | 6720 |
| CAACCAAGTC | ATTCTGAGAA | TAGTGTATGC | GGCGACCGAG | TTGCTCTTGC | CCGGCGTCAA | 6780 |
| TACGGGATAA | TACCGCGCCA | CATAGCAGAA | CTTTAAAAGT | GCTCATCATT | GGGAAACGTT | 6840 |
| CTTCGGGGCG | AAAACTCTCA | AGGATCTTAC | CGCTGTTGAG | ATCCAGTTCG | ATGTAACCCA | 6900 |
| CTCGTGCACC | CAACTGATCT | TCAGCATCTT | TTACTTTCAC | CAGCGTTTCT | GGGTGAGCAA | 6960 |
| AAACAGGAAG | GCAAAATGCC | GCAAAAAAGG | GAATAAGGGC | GACACGGAAA | TGTTGAATAC | 7020 |
| TCATACTCTT | CCTTTTTCAA | TATTATTGAA | GCATTTATCA | GGGTTATTGT | CTCATGAGCG | 7080 |
| GATACATATT | TGAATGTATT | TAGAAAAATA | AACAAATAGG | GGTTCCGCGC | ACATTTCCCC | 7140 |
| GAAAAGTGCC | ACCTGACGTC | TAAGAAACCA | TTATTATCAT | GACATTAACC | TATAAAAATA | 7200 |
| GGCGTATCAC | GAGGCCCTTT | CGTC | | | | 7224 |

( 2 ) INFORMATION FOR SEQ ID NO:6:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

| | | | | | |
|---|---|---|---|---|---|
| ACGTTACTGG | TTTAACCTTC | CTCTTCTTCT | TAGGCATGGT | GGGAGGGTAC | CTCTAGA | 57 |

( 2 ) INFORMATION FOR SEQ ID NO:7:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

| | | | | | |
|---|---|---|---|---|---|
| ATTGCGTTGC | GCAACCTTTC | ACCTCTTCTT | CTTAGGAGGC | CTCAGGCTGC | TCTGCCCGCT | 60 |
| TTCCAG | | | | | | 66 |

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

ACAAGGCAAG ACTAGTCCGA CAATTG                      26

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TTTAAGTGCC TACTAGTATA CAATAAA                     27

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

AATATAAAAT TTACTAGTGT ATAATGTGTT                 30

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CTCCTGGTGG ACTAGTTCAA AGAACT                      26

( 2 ) INFORMATION FOR SEQ ID NO:12:

( i ) SEQUENCE CHARACTERISTICS:

(A) LENGTH: 43 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CTAGGGTCGA CTGTGGAATT GTGAGCGCTC ACAATTCCAC AAC                43

(2) INFORMATION FOR SEQ ID NO:13:

(i) SEQUENCE CHARACTERISTICS:
                (A) LENGTH: 43 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

CTAGGTTGTG GAATTGTGAG CGCTCACAAT TCCACAGTCG ACC                43

(2) INFORMATION FOR SEQ ID NO:14:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

CIAGGGTCGA CATTGTGAGC GCTCACAATC                                30

(2) INFORMATION FOR SEQ ID NO:15:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

CTAGGATTGT GAGCGCTCAC AATGTCGACC                                30

1

NUCLEIC ACID CONSTRUCT ENCODING A NUCLEAR TRANSPORT PEPTIDE OPERATIVELY LINKED TO AN INDUCIBLE PROMOTER

CROSS REFERENCE TO RELATED APPLICATION

This application is a continuation of U.S. application Ser. No. 07/640,983, now abandoned, filed Jan. 14, 1991, the disclosures of which are hereby incorporated by reference.

TECHNICAL FIELD

The present invention relates to a system for regulating expression of eukaryotic genes in cells, both in vitro and in vivo, using exogenously added inducers. The invention also relates to transgenic animals containing the regulated eukaryotic genes.

BACKGROUND

The present invention employs an inducible bacterial repressor proteins to block transcription of an exogenously-added gene in mammalian cells. The addition of exogenous inducer substances to the cells induces the repressor thus removing the block to transcription and derepressing expression of the exogenously-added gene. Both the lexA and lac repressor have been used in mammalian cells to control gene expression. See for example, Brown et al., Cell 49:603–612 (1987); Hu et al., Cell, 48:555–566 (1987); and Smith et al., EMBO J., 7:3975–3982 (1988).

Chimeric gene constructions have been prepared in which the lac repressor is used to inhibit expression of the simian virus 40 (SV40) early promoter, a vaccinia virus promoter, or a T3 bacteriophage in mammalian cells where the promoter contains appropriately placed operators (the repressor recognition sequences). In these systems, repression is removed by the addition of a lac inducer, typically isopropyl-β-D-thiogalactoside (IPTG). Brown et al., supra: Figge et al., Cell, 52:713–722 (1988); Fuerst et al., Proc. Natl. Acad. Sci. U.S.A., 86:2549–2553 (1989); and Hu et al., supra. However, induction by the addition of IPTG did not produce necessary increases in the level of gene expression of the promoter-controlled eukaryotic gene when present in the form of a stably integrated gene in a eukaryotic cell.

An alternative expression system involved preparation of a chimeric protein having the specificity of a bacterial repressor and the induction capacity of a mammalian transactivator protein. The first reported chimeric protein comprised the lexA DNA-binding protein and the activation domain of the yeast transcription factor, GAL4. Brent et al., Cell, 43:719–736 (1985). More recently a chimeric regulatory protein was produced containing the E. coli lac repressor that was modified to include a nuclear localization signal from the simian 40 (SV40) large tumor antigen and was fused with the transcription activation domain from the herpes simplex virus type 1 virion protein 16. This chimeric protein, called lac activator protein (LAP), was a potent activator of promoters containing lac operator sequences positioned either upstream or downstream from the transcription unit. See Lapow et al., Mol. Cell. Biol., 10:3343–3356 (1990). The uninduced LAP protein is not a repressor but rather acts as an activator of gene expression until induced by an inducer. The LAP protein, although expressed in a target cell's cytoplasm and transported to the nucleus where it activates a target gene, is not an expression system in which gene transcription is enhanced through the use of endogenously added inducers or other externally imposed regulatory switch mechanisms.

BRIEF SUMMARY OF THE INVENTION

A system has now been developed that allows the specific regulation of exogenous added genes to a cell present either in vitro or in vivo in a transgenic animal, whereby the addition of inducer to the cells derepresses the transcription of the preselected gene, resulting in switch activation of the gene's expression.

In one embodiment, the present invention contemplates a fusion protein comprising a nuclear transport signal amino acid residue sequence operatively linked to an inducible repressor amino acid residue sequence.

The present invention also contemplates a recombinant nucleic acid molecule coding for a nucleus-targeted inducible repressor polypeptide comprising a nuclear transport signal-coding nucleic acid segment operatively linked to an inducible repressor-coding nucleic acid segment.

Also contemplated is a eukaryotic cell comprising at least one lac operator-containing nucleic acid segment operatively linked to a promoter-containing nucleic acid segment and a fusion protein comprising a nuclear-transport signal amino acid residue sequence operatively linked to an inducible repressor amino acid residue sequence capable of binding said lac operator.

In another embodiment, the present invention contemplates a transgenic mammal having somatic and germ cells containing a recombinant nucleic acid molecule coding for a nucleus-targeted inducible repressor polypeptide comprising a nuclear transport signal-coding nucleic acid segment operatively linked to an inducible repressor-coding nucleic acid segment.

Further contemplated is a modified thiogalactoside having the formula: R-betz-D-thiogalactoside where R has the formula cyclohexyl, 2-[1,3-diamino]propyl, 4-amino-1-butyl, 3-amino-1-propyl, 3-carboxyl-1-propyl, n-butyl, n-pentyl, n-propyl, 3-phosphato-1-propyl, ethyl, isobutyl, or 2-nitrilo-ethyl.

The regulatory control of exogenous genes in vivo or in vitro provides a wide variety of commercial and research applications. Transgenic animals containing an exogenously-added regulatable gene provide a research tool to investigate the control of eukaryotic genes, allow the preparation of animals with altered growth characteristics, allow the development of animal models for human disease gene therapy, and provides a system to study developmental genes and tumorigenesis. Inducible expression systems are particularly useful because they allow for precise regulation of the exogenous gene without altering the expression of the other genes present in a cell.

BRIEF DESCRIPTION OF THE DRAWINGS

In the drawings, forming a portion of this disclosure.

DETAILED DESCRIPTION OF THE INVENTION

A. Definitions

Figure 1:
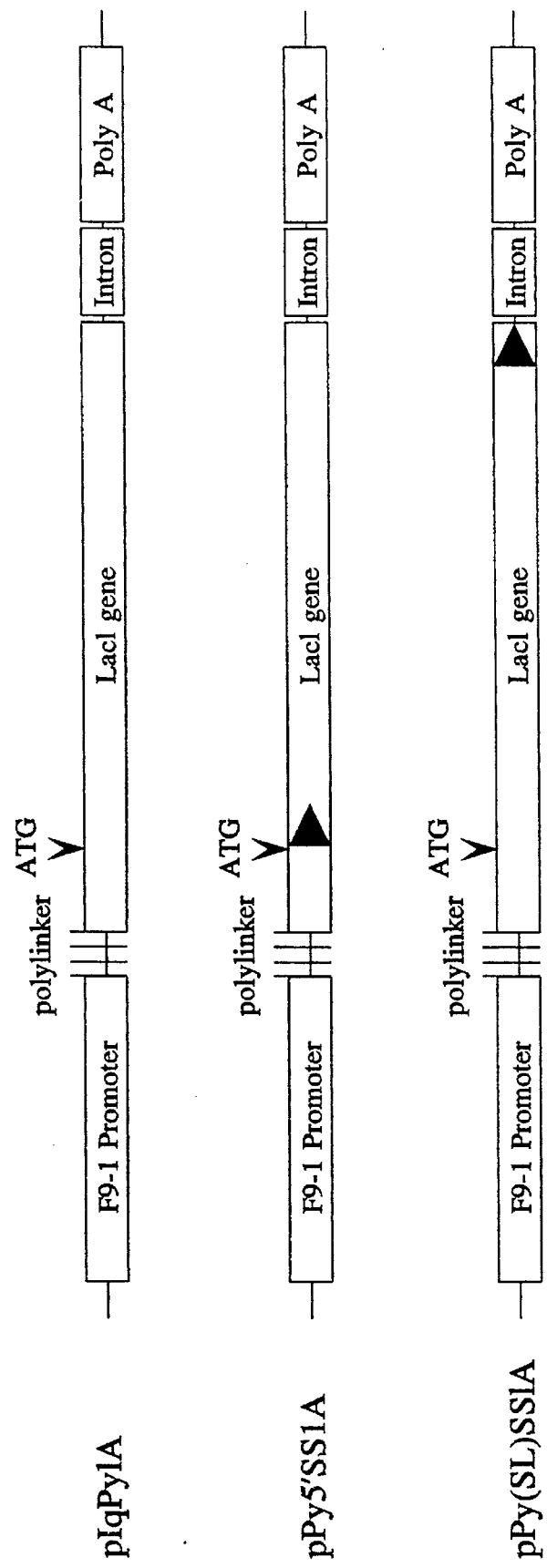
In FIG. 1, a schematic of the various features of the expression vector containing a nucleus-targeted inducible repressor polypeptide is shown. The F9-1 promoter segment, the Lac I gene, the SV40 intron and the SV40 polyadenylation signal is shown. The initiation codon (ATG) for the lac I gene and the nuclear transport signal (diamond) are also shown.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |

-continued

| TABLE OF CORRESPONDENCE | | |
|---|---|---|
| SYMBOL | | |
| 1-Letter | 3-Letter | AMINO ACID |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 C.F.R. 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH$_2$ or acetyl or to a carboxy-terminal group such as COOH.

Base Pair: a partnership of adenine (A) with thymine (T), or of cytosine (C) with guanine (G) in a double-stranded DNA molecule. In RNA, uracil (U) is substituted for thymine. Base pairs are said to be "complementary" when their component bases pair up normally when a DNA or RNA molecule adopts a double-stranded configuration.

Complementary Nucleotide Sequence: a sequence of nucleotides in a single-stranded molecule of DNA or RNA that is sufficiently complementary to another single strand to specifically (non-randomly) hybridize to it with consequent hydrogen bonding.

Conserved: a nucleotide sequence is conserved with respect to a preselected (reference) sequence if it non-randomly hybridizes to an exact complement of the preselected sequence.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Fusion Protein: A protein comprised of at least two polypeptides and a linking sequence to operatively link the two polypeptides into one continuous polypeptide. The two polypeptides linked in a fusion protein are typically derived from two independent sources, and therefore a fusion protein comprises two linked polypeptides not normally found linked in nature.

Gene: a nucleic acid whose nucleotide sequence codes for a RNA, DNA or polypeptide molecule. Genes may be uninterrupted sequences of nucleotides or they may include such intervening segments as introns, promoter regions, splicing sites and repetitive sequences. A gene can be either RNA or DNA.

Hybridization: the pairing of complementary nucleotide sequences (strands of nucleic acid) to form a duplex, heteroduplex, or complex containing more than two single-stranded nucleic acids, by establishing hydrogen bonds between/among complementary base pairs. Hybridization is a specific, i.e., non-random, interaction between/among complementary polynucleotides that can be competitively inhibited.

Linking Sequence: an amino acid residue sequence comprising one to seven amino acid residues. A linking sequence serves to chemically link two disparate polypeptides via a peptide bond between the linking sequence and each of the polypeptides.

Nucleotide: a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Nucleotide Analog: a purine or pyrimidine nucleotide that differs structurally from an A, T, G, C, or U base, but is sufficiently similar to substitute for the normal nucleotide in a nucleic acid molecule. Inosine (I) is a nucleotide analog that can hydrogen bond with any of the other nucleotides, A, T, G, C, or U. In addition, methylated bases are known that can participate in nucleic acid hybridization.

Polynucleotide: a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Polypeptide or Peptide or Protein: a linear series of at least two amino acid residues in which adjacent residues are connected by peptide bonds between the alpha-amino group of one residue and the alpha-carboxy group of an adjacent residue.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more proteins are referred to herein as "expression vectors". Particularly important vectors allow cloning of cDNA (complementary DNA) from mRNAs produced using reverse transcriptase.

B. Nucleus-targeted Inducible Repressors

A nucleus-targeted inducible repressor polypeptide of the present invention is a polypeptide comprising a nuclear transport signal amino acid residue sequence operatively linked to an inducible repressor amino acid residue sequence. By "operatively linked" is meant that the two amino acid residue sequences are joined by a peptide bond between a terminal amino acid residue in each sequence, to form a single amino acid residue sequence. Thus a nucleus-targeted inducible repressor polypeptide is a protein comprising two functional elements defined by the two operatively linked amino acid residue sequences, and is also referred to as a fusion protein.

A nuclear transport signal amino acid residue sequence, or nucleus-targeting sequence, is an amino acid residue sequence that, when present in a protein, directs migration of that protein to the cell's nucleus, as evidenced by accumulation of the protein in the nucleus after biosynthesis in the cell's cytoplasm. Nucleus-targeting sequences have been described for a variety of proteins and typically are short amino acid residue sequences of about 5–15 residues.

The SV40 Large T antigen was found to contain a seven amino acid residue sequence that defines a minimum region of the Large T antigen required for nuclear targeting. Kalderon et al., *Cell*, 39:499–509 (1984). The seven amino acid residue sequence shown in SEQ ID No. 1 corresponds to residues 126 through 132 of SV40 Large T antigen and is referred to in the published literature as a nuclear location signal (NLS).

The SV40-derived nuclear location signal has been engineered into several different proteins to cause them to accumulate in the nucleus of a cell, including bacteriophage T7 RNA polymerase into mammalian cell nuclei (Dunn et al., *Gene*, 68:259–266, 1988), and into yeast cell nuclei (Benton et al., *Mol. Cell. Biol.*, 10:353–360, 1990).

Adenovirus E1a gene product contains a five amino acid residue NLS sequence shown in SEQ ID No. 2 that is located at the extreme carboxyl terminus of E1a. Lyons et al., *Mol. Cell. Biol.*, 7:2451–2456 (1987). Other NLS sequences have been identified in both higher eukaryotes and in the yeast, *Saccharomyces cerevisiae*. See, for example, the review by Silver et al., in Protein Transfer and Organelle Biogenesis", Das et al., eds., Academic Press, Inc., N.Y., P. 747–769 (1988).

Although the SV40 nuclear location sequence is used as exemplary herein of a nucleus targeting sequence, other nuclear location sequences can be utilized, whether identified presently or in the future. Assays for identifying proteins and protein regions having a nucleus-targeting sequence have been described. See, for example Parnaik et al., *Mol. Cell. Biol.*, 10:1287–1292 (1990).

An inducible repressor amino acid residue sequence is a sequence of amino acid residues that forms a functional protein domain having the capacity to specifically bind to a nucleic acid operator present in a structural gene transcription unit that, when bound, represses transcription of the structural gene. The repressor protein is an inducible repressor if, upon binding to a specific inducer, the repressor protein disassociates from the operator to which it was bound thereby permitting transcription of the structural gene to occur.

A nucleic acid operator or operator is a sequence of nucleotides in, for example, a transcription unit that has the capacity to specifically bind a specific repressor protein. The repressor and operator form a system for regulation of the specific gene in a particular structural gene transcription unit by the action of the specific inducer on the repressor. The system of genes comprising a repressor gene, operator gene and the regulated structural gene are referred to as an operon, are well characterized and are known for the specific interaction between the members of the system.

The prototypical inducible repressor is the lac repressor, extensively characterized and described at least in "The Operon" Miller et al., Cold Spring Harbor Laboratory, New York (1980). Inducers for the lac repressor are galactosides, and are preferably the thiogalactoside derivatives described further herein.

Although the lac repressor, and its related components the lac operator and inducers of the lac repressor, are used as exemplary in the present invention, the invention is not so limited. Other repressor-operator-inducer systems derived from other operons can be used according to the basic teachings of the present invention.

C. Recombinant DNA Molecules

In one embodiment the present invention contemplates a recombinant deoxyribonucleic acid (DNA) molecule (rDNA) that encodes a nucleus-targeted inducible repressor polypeptide.

Thus, in one embodiment of this invention a rDNA that encodes a nucleus-targeted inducible repressor polypeptide contains two DNA segments that are operatively linked to form a single polypeptide having the two functional elements of the before-described fusion protein. The first DNA segment encodes a nuclear transport signal amino acid residue sequence and the second DNA segment encodes an inducible repressor amino acid residue sequence.

The operative linkage of two DNA segments in the context of an rDNA that encodes a fusion protein requires that the reading frame of the first DNA segment be the same as the reading frame of the second DNA segment such that the resulting rDNA encodes a fusion protein having both functional domains. The operative linker therefore can be a phosphodiester bond between adjacent nucleotides of the rDNA molecule or it can be a spacer oligonucleotide that preserves the reading frame between the two DNA segments.

The location of a nucleus-targeting sequence relative to the inducible repressor amino acid residue sequence in a fusion protein of this invention can vary, so long as the fusion protein exhibits the requisite properties. As is well known in the fusion protein arts where functional domains of different proteins are operatively linked, there are some orientations of the elements that have greater activity than others.

For example, the present invention describes two preferred rDNA embodiments that encode a fusion protein where the nucleus-targeting sequence is located in the 5' terminal region of the fusion protein or is in the 3' terminal region of the fusion protein. In the design of these two embodiments, five constructs were initially produced, one having the nucleus-targeting sequence in the 5' terminal region and four having the nucleus-targeting region in the 3' terminal region. Of these five constructions, four of the rDNA molecules produced fusion proteins that function as inducible repressors when measured in the bacterial IPTG spot assay described in Example 1B. Of the four constructs, two were selected for preparation of a rDNA that expresses protein in a eukaryotic vector. Both constructs were able to express a fusion protein that is targeted to the nucleus when assayed as described in Example 3A. Thus, by screening for the desired properties according to the assays described herein, other functional fusion proteins can readily be prepared.

In preferred embodiments the 5' terminal location of a nucleus-targeting sequence is within about 5 amino acid residues of the amino terminus of the inducible lac repressor. Particularly preferred is a construct where the nucleus-targeting sequence begins as the second amino acid residue after the amino-terminal methionine encoded by the initiation codon (ATG). This embodiment is shown in the rDNA molecule pPy5'SS1A.

In other preferred embodiments the 3' terminal location of a nucleus-targeting sequence is within the region of the 3' terminal 200 bases located upstream from the termination codon of the DNA segment that codes for the inducible lac repressor. Particularly preferred are rDNA molecules where the nucleus-targeting sequence is operatively linked by a spacer oligonucleotide to the 5' terminal codon prior to a termination codon. Exemplary is the rDNA molecule pPy(SL)SS1A.

In the selection of the location of the nucleus-targeting sequence relative to the inducible repressor in a fusion protein, it is required to maintain inducible repressor activity in the fusion protein. Typical locations for operatively linking the nucleus-targeting sequence are the amino- or carboxy-terminal portions of the inducible repressor amino acid residue sequence, away from the major central portion of the repressor sequence that, when folded into the protein's tertiary structure, forms either the operator binding site (DNA binding domain of the repressor) or the inducer binding site on the repressor.

In another embodiment the present invention contemplates a rDNA molecule that encodes an operator-regulated reporter polypeptide.

A reporter polypeptide is an amino acid residue sequence that has a detectable quality, such that the detection of that quality indicates (reports) the presence of the polypeptide. Exemplary reporter polypeptides are proteins that confer drug resistance to a host cell containing the protein, such as those that confer resistance to ampicillin (Amp R), tetracycline (Tet R), hygromycin (Hyg R), neomycin (Neo R), chloramphenicol (Cam R), and the like. Other exemplary reporter polypeptides are proteins that produce a detectable signal, such as an enzyme that produces a detectable product in the presence of the appropriate substrate. Exemplary of this class of reporter polypeptide is the enzyme luciferase, derived from the firefly *Photinus pyralis,* which produces light photons. The gene that encodes the luciferase enzyme has been cloned (De Wet et al., *Mol. Cell. Biol.,* 7:7250737, 1987) and is used herein in a rDNA of this invention to encode a preferred reporter polypeptide. Particularly preferred rDNA molecules that encode a luciferase reporter polypeptide are the rDNA plasmids p200-402, pNS3P and pl00-223.

A rDNA molecule that encodes an operator-regulated reporter polypeptide contains an operator-regulated gene expression DNA segment operatively linked to a DNA segment having a structural gene that encodes the reporter polypeptide such that when the expression segment is up-regulated for transcription (i.e., switched on by induction), the linked structural gene is expressed producing the reporter polypeptide.

An operator-regulated gene expression segment is a DNA segment that comprises at least one operator-containing DNA segment operatively linked to a promoter-containing DNA segment such that the operator-containing DNA segment regulates the ability of the promoter-containing DNA segment to initiate transcription.

A promoter is a sequence of nucleotides that forms an element of a structural gene transcriptional unit which controls the gene's expression by providing a site for RNA polymerase binding resulting in the initiation of the process of transcription whereby a gene is transcribed to form a messenger ribonucleic acid (mRNA) molecule. Promoters can be regulatable (modulated) or they can be constitutive (constant). Regulatable promoters are generally well characterized and have the capacity to respond to stimuli such as various DNA binding proteins as is well known. See, for example "Promoters: Structure and Function", Rodriguez et al., eds., Praeger Press, New York (1982).

In addition, a regulatable promoter can be modulated by external stimuli such as compositions, light, heat, stress and the like. Inducible, suppressible and repressible promoters are regulatable promoters. Tissue specific promoters may also be regulatable promoters. The tissue specific promoter directs the expression of that gene to a specific cell type. The tissue specific promoter causes the gene located 3' of it to be expressed predominantly, if not exclusively in the specific cells where the promoter expressed its endogenous gene. Typically, it appears that if a tissue-specific promoter expresses the gene located 3' of it at all, then it is expressed appropriately in the correct cell types as has been reviewed by Palmiter et al., Ann. Rev. Genet., 20:465–499 (1986). When a tissue specific promoter is controlling the expression of a gene, that gene will be expressed in a small number of tissues or cell types rather than in substantially all tissues and cell types. Examples of tissue specific promoters include the immunoglobulin promoter described by Brinster et al., Nature, 306:332–336 (1983) and Storb et al., Nature, 310:238–231 (1984); the elastase-I promoter described by Swift et al., Cell, 38:639–646 (1984); the globin promoter described by Townes et al., Mol. Cell. Biol., 5:1977–1983 (1985), and Magram et al., Mol. Cell. Biol., 9:4581–4584 (1989), the insulin promoter described by Bucchini et al., Proc. Natl. Acad. Sci., USA, 83:2511–2515 (1986) and Edwards et al., Cell, 58:161 (1989); the immunoglobulin promoter described by Ruscon et al., Nature, 314:330–334 (1985) and Grosscheld et al., Cell, 38:647–658 (1984); the alpha actin promoter described by Shani, Mol. Cell. Biol., 6:2624–2631 (1986); the alpha crystalline promoter described by Overbeek et al., Proc. Natl. Acad. Sci. USA, 82:7815–7819 (1985); the prolactin promoter described by Crenshaw et al., Genes and Development, 3:959–972 (1989); the proopiomelanocortin promoter described by Tremblay et al., Proc. Natl. Acad. Sci., USA, 85:8890–8894 (1988); the beta thyroid stimulating hormone (BTSH) promoter described by Tatsumi et al., Nippon Rinsho, 47:2213–2220 (1989); the mouse mammary tumor virus (MMTV) promoter described by Muller et al., Cell, 54:105 (1988); the albumin promoter described by Palmiter et al., Ann. Rev, Genet., 20:465–499 (1986); the Keratin promoter described by Vassar et al., Proc. Natl. Acad. Sci., USA., 86:8565–8569 (1989); the osteonectin promoter described by McVey et al., J. Biol. Chem., 263:11,111–11,116 (1988); the prostate-specific promoter described by Allison et al., Mol. Cell. Biol., 9:2254–2257 (1989); the opsin promoter described by Nathans et al., Proc. Natl. Acad. Sci., USA, 81:4851–4855 (1984); the olfactory marker protein promoter described by Danciger et al., Proc. Natl. Acad. Sci., USA, 86:8565–8569 (1989); the neuron-specific enolase (NSE) promoter described by Forss-Pelter et al., J. Neurosci. Res., 16:141–151 (1986); the L-7 promoter described by Sutcliffe, Trends in Genetics, 3:73–76 (1987) and the protamine 1 promoter described Peschon et al., Ann. New York Acad. Sci., 564:186–197 (1989) and Braun et al., Genes and Development, 3:793–802 (1989). See Table I for the tissue specificity of the promoters.

TABLE I

Tissue Specific Promoters

| Gene | Species | Tissue Specificity[1] | Ref.[2] |
|---|---|---|---|
| α-Actin | Rat | mu, he | A |
| α-Actin | Rat | te, th, lu | A |
| Elastase - I | Rat | Pa | B |
| α-Fetoprotein | Mouse | ys, li | C |
| β-Globin | Human | ery | D |
| β-Globin | Rabbit | te, mu | E |
| β-Globin | Rabbit | ery | F |
| τ⁶-Globin | Human | ery | G |
| α¹-Globin | Mouse | br | H |
| Growth hormone | Human | pit | I |
| Immunoglobin-k | Mouse | B | J |
| Immunoglobin-μ | Mouse | B, T | K |
| Insulin | Human | B-cells | L |
| Myosin Light Chain-2 | Rat | mu | M |
| Protamine 1 | Mouse | te | N |
| α-A-crystallin | trans | lens | O |
| Prolactin | | pit | P |
| Proopiomelanacortin | | pit | Q |
| BTSH | | | R |
| MMTV | Mouse | breast | S |
| Albumin | | li | T |
| Keratin | | skin | U |
| Osteonectin | | bone | V |
| Prostate | | prostate | W |
| Olfactory Marker Protein | | neuron | X |
| NSE | | neuron | Y |
| L-7 | | neuron | Z |
| Opsin | | retina | A1 |

[1]Abbreviations: br, brain; B, lymphocytes; mu, skeletal muscle; he, cardiac muscle; te, testis; beta, beta cells; th, thymus; lu, lung; Pa, exocrine pancreas; ys, yolk sac; li, liver; ery, erythroid cells; pit, pituitary and lens, eye lens.
[2]References:
A — Shani, Mol. Cel. Biol., 6:2624–31 (1986).
B — Swift et al., Cell, 38:639–649 (1984).
C — Krumlauf et al., Nature, 319:224–226 (1985).
D — Townes et al., EMBO J., 4:1715–1723 (1985).
E — Lacy et al., Cell, 34:343–348 (1983).
F — Wagner et al., Proc. Natl. Acad. Sci., USA, 78:6376–6380 (1981).
G — Brinster et al., Nature, 283:499–501 (1980).
H — Rusconi et al., in The Impact of Gene Transfer Techniques in Eukaryotic Cell Biology, ed. J. S. Schell et al., pp 134–152, Berlin: Springer Verlag (1984).
I — Behringer et al., Genes Dev., 2:453 (1988).
J — Storb et al., Nature, 310:238–241 (1984).
K — Grosschedl et al., Cell, 38:647–658 (1984).
L — Selden et al., Nature, 321:545–528 (1986).
M — Shani, Nature, 314:283–286 (1985).
N — Peschon et al., Ann. N. York Acad, Sci., 564:186–197 (1989).
O — Breitman et al., Dev., 106:457–463 (1989).
P — Crenshaw et al., Genes and Development, 3:959–972 (1989).
Q — Trembllay et al., Proc. Natl. Acad. Sci., USA, 85:8890–8894 (1988).
R — Tatsumi et al., Nippon Rinsho, 47:2213–2220 (1989).
S — Muller et al., Cell 54:105 (1988).
T — Palmiter et al., Ann. Rev. Genet., 20:465–499 (1986).
U — Vassar et al., Proc. Natl. Acad. Sci., USA, 86:8565–8569 (1989).
V — McVey et al., J. Biol. Chem., 263:11,111–11,116 (1988).
W — Allison et al., Mol. Cell. Biol., 9:2254–2257 (1989).
X — Danciger et al., Proc. Natl. Acad. Sci., USA, 86:8565–8569 (1989).
Y — Forss-Petter et al., J. Neurosci. Res., 16:141–151 (1986).
Z — Sutcliffe, Trends in Genetics, 3:73–76 (1987).
A1 — Nathans et al., Proc. Natl. Acad. Sci., USA, 81:4851–4855 (1984).

In addition to a promoter-containing segment, an operator-regulated gene expression DNA segment contains an operator-containing DNA segment.

An operator-containing DNA segment is a DNA segment that comprises at least one operator. An operator is a sequence of nucleotides that forms a site for specific repressor binding. Thus, operators are specific for a particular repressor.

A repressor binding site is considered specific if the equilibrium binding constant for repressor binding to the operator is greater than $10^{-9}$ molar (M), preferably greater than $10^{-10}$M, and more preferably greater than $10^{-11}$M. The equilibrium binding constant for a repressor binding to an operator can readily be measured by well known equilibrium dialysis methods, or in a nitrocellulose filter binding assay where repressor is immobilized on nitrocellulose and $^{32}$P-labeled operator-containing DNA segment is presented in solution for binding to the immobilized repressor. See, Miller "Experiments in Molecular Genetics", p367–370, Cold Spring Harbor Laboratory, New York, 1972.

The operator for the lac repressor has been well characterized and is used as exemplary herein. See Miller et al., in "The Operon", Cold Spring Harbor Laboratory, New York (1980), for a detailed study. Alternative nucleotide sequences have been described for a lac repressor operator that specifically binds to repressor. See, for example, the description of numerous lac operator variants and the methods for characterizing their repressor-binding activity reported by Sartorius et al., EMBO J., 8:1265–1270 (1989); and Sadler et al., Proc. Natl. Acad. Sci. USA, 80:6785–6789 (1983). Any nucleotide sequence that binds lac repressor specifically can be used in the present invention, although wild type and optimized operators are preferred and used as exemplary herein. The two optimized operators derived from the lac operon include the nucleotide sequences shown in SEQ. ID No. 3 and No. 4 as follows:
(SEQ. ID NO. 3) 5'-TGT GGA ATT GTG AGC GCT CAC AAT TCC ACA-3'
(SEQ. ID NO. 4) 5'-ATT GTG AGC GCT CAC AAT-3'

Operators function to control the promoter for a structural gene by a variety of mechanisms. The operator can be positioned within a promoter such that the binding of the repressor covers the promoter's binding site for RNA polymerase, thereby precluding access of the RNA polymerase to the promoter binding site. Alternatively, the operator can be positioned downstream from the promoter binding site, thereby blocking the movement of RNA polymerase down through the transcriptional unit.

Multiple operators can be positioned on a rDNA molecule to bind more than one repressor. The advantage of multiple operators is several fold. First, tighter blockage of RNA polymerase binding or translocation down the gene can be effected. Second, when spaced apart by at least about 70 nucleotides and typically no more than about 1000 nucleotides, and preferably spaced by about 200 to 500 nucleotides, a loop can be formed in the nucleic acid by the interaction between a repressor protein bound to the two operator sites. The loop structure formed provides strong inhibition of RNA polymerase interaction with the promoter, if the promoter is present in the loop, and provides inhibition of translocation of RNA polymerase down the transcriptional unit if the loop is located downstream from the promoter.

Typically a DNA segment of this invention is no more than about 100,000 and preferably no more than 10,000 nucleotides (bases) in length.

A DNA segment of the present invention can easily be synthesized by chemical techniques, for example, via the phosphotriester method of Matteucci et al., J. Am. Chem. Soc., 103:3185 (1981) or using phosphoramidite chemistry according to Beaucage et al., M. H. Tetrahedron Letters, 22:1859–1862 (1982). Of course, by chemically synthesizing the coding sequence, any desired modifications can be made simply by substituting the appropriate bases for those in the native nucleotide base sequence.

The DNA segments of the present invention typically are duplex DNA molecules having cohesive termini, i.e., "overhanging" single-stranded portions that extend beyond the double-stranded portion of the molecule. The presence of cohesive termini on the DNA molecules of the present invention is generally preferred.

Larger DNA segments corresponding to, for example, complete structural genes or whole transcriptional units that include promoters, introns and exons in the form of a "cassette", i.e. having convenient restriction enzyme site-defined cohesive termini, can easily be prepared by ligating smaller oligonucleotides. Typically, single stranded oligonucleotides of between 40–75 nucleotide bases in length are prepared with overlapping complementary ends to form the complete cassette DNA segment. The oligonucleotides are then annealed and the oligos are ligated to form a complete double stranded (ds DNA) molecule. See for example, Urdez et al., Proc. Natl. Acad. Sci. USA, 80:7461–7465 (1983); and Hallewell et al., J. Biol. Chem., 264:5260–5268 (1989).

Also contemplated as within the present invention are ribonucleic acid (RNA) equivalents of the above described DNA segments.

D. Expression Vectors

A preferred rDNA of this invention comprises a DNA segment of the present invention operatively linked to a vector for expression of the structural gene product contained in the DNA segment. This preferred rDNA, referred to as an expression vector, is characterized as being capable of directly expressing, in a compatible host, a structural gene product such as a repressor protein or a reporter protein of the present invention. By "directly expressing" is meant that the mature polypeptide chain of the expressed structural gene product is formed by translation alone as opposed to proteolytic cleavage of two or more terminal amino acid residues from a larger translated precursor protein.

A preferred rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. As used herein, the term "operatively linked", in reference to DNA segments, describes that the nucleotide sequence is joined to the vector so that the sequence is under the transcriptional and/or translation control of the expression vector and can be expressed in a suitable host cell.

In one embodiment, the present invention contemplates an expression vector for expressing a nucleus-targeted inducible repressor polypeptide. Such a vector comprises a rDNA of this invention that encodes a nucleus-targeted inducible repressor polypeptide operatively linked to a vector as described herein.

Preferred repressor expression vector of this type contain an F9-1 promoter for expressing the nucleus-targeted inducible repressor polypeptide, and/or SV40 intron and poly A tail encoding DNA segments located to form a transcription unit capable of expressing the polypeptide in mammalian cells. Exemplary are the expression vectors pPy5'SS1A and pPy(SL)SS1A described herein.

In another embodiment, the present invention contemplates an expression vector for expressing an operator-regulated reporter polypeptide. Such a vector comprises a rDNA of this invention that encodes an operator-regulated reported polypeptide operatively linked to a vector as described herein.

Preferred reporter protein expression vectors of this type contain an RSV promoter for expressing the reporter polypeptide, preferably a luciferase protein, and further include the genetic elements of a transcriptional start site, an exon, an intron and poly A tail encoding DNA segments arranged substantially as found, for example, in the rDNA molecule pRSVLuc described in SEQ. ID No. 5. Particularly preferred and exemplary are the expression vectors pPy5'SS1A and pPy(SL)SS1A described herein.

Insofar as it is convenient in some applications to provide an expression vector whereby a variety of preselected reporter polypeptides can be inserted into the vector for expression, it is contemplated that an expression vector can be first prepared without a reporter polypeptide encoding DNA segment, but does contain convenient restriction sites positioned such that a reporter gene in the form of a DNA segment with preselected cohesive termini can be inserted into the vector for expression under the control of the operator-regulated gene expression DNA segment.

For example, a preferred expression vector comprising an operator-regulated gene expression DNA segment is prepared by removing the luciferase reporter gene DNA segment from any one of the rDNA's pR00-402, pNS3P or pI00-223 corresponding to the nucleotide base sequence of the luciferase gene between bases 2975 and 4822 of SEQ. ID No. 5 (pRSVLuc), and inserting in its place a polylinker sequence that provides convenient restriction sites for inserting a preselected reporter gene-encoding DNA segment.

Typical promoters that express a structural gene without substantial restriction as to tissue or cell type are referred to as ubiquitous promoters and represent a preferred class of promoters. Exemplary ubiquitous promoters are the thymidine kinase (TK) promoter obtained from Herpes Simplex Virus (HSV), the F9-1 promoter obtained from Polymera Virus cells, and the Rous Sarcoma Virus (RSV) promoter. The RSV promoter is present in the rDNA's pRSVLuc, pR00-402, pNS3P and PI00-223 described herein. The F9-1 promoter is present in the rDNA's pI$^q$Py1A, pPy5'SS1A and pPy(SL)SS1A described herein.

As is well known in the art, the choice of vector to which a DNA segment of the present invention is operatively linked depends upon the functional properties desired, e.g., the host cell in which the DNA is to be propagated and the host cell selected for expressing the gene product. These limitations are inherent in the art of constructing recombinant DNA molecules. However, a vector contemplated by the present invention is at least capable of directing the replication, and preferably also expression, of a structural gene operatively linked to the vector.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art and include OriC as described herein. In addition, those embodiments that include a procaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin as used herein, tetracycline, kanamycin, and the like.

Those vectors that include a procaryotic replicon may also include a procaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Bacterial expression systems, and choice and use of vectors in those systems is described in detail in "Gene Expression Technology", *Meth. Enzymol.*, Vol 185, Goeddel, Ed., Academic Press, N.Y. (1990). Typical of such vector plasmids are pUC8, pUC9, pBR322 and pBR329 available from Bio-Rad Laboratories, (Richmond, Calif.) and pPL and pKK233-2, available from Pharmacia, (Piscataway, N.J.), or Clone Tech (Palo Alto, Calif.).

Expression vectors compatible with eukaryotic cells, preferably those compatible with vertebrate cells, can also be used to form the recombinant DNA molecules of the present invention. Eukaryotic cell expression vectors are well known in the art and are available from several commercial sources. Typically, such vectors are provided containing convenient restriction sites for insertion of the desired gene. Typical of such vectors are pSVL and pKSV-10 (Pharmacia), pBPV-1/pML2d (International Biotechnologies, Inc.), and pTDT1 (ATCC, #31255).

In preferred embodiments, the eukaryotic cell expression vectors used to construct the recombinant DNA molecules of the present invention include a selectable phenotypic marker that is effective in a eukaryotic cell, such as a drug resistance selection marker or selective marker based on nutrient dependency. A preferred drug resistance marker is the gene whose expression results in neomycin resistance, i.e., the neomycin phosphotransferase (neo) gene. (Southern et al., *J. Mol. Appl. Genet.*, 1:327–341, 1982), or hygromycin resistance, i.e., the hygromycin resistance gene.

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eukaryotic cells. The construction and use of retroviral vectors has been described at least by Sorge et al., *Mol. Cell. Biol.*, 4:1730–37 (1984).

Other virus-based expression systems can be used, as is well known, including systems based on SV-40, Epstein-Barr, Vaccinia, and the like. See, for example, "Gene Expression Technology", (supra), at pp.485–569. For expression in yeast, a variety of vector are known in the art, in particular the vector, pC1/1 described by Brake et al., Proc. Natl. Acad. Sci. USA, 81:4642–4647 (1984); and Hallewell et al., *Biotechnology*, 5:363–366 (1987). Other vectors are described in "Gene Expression Technology", (supra).

Preferably the vectors employed herein will contain multiple restriction sites to allow convenient insertion of a DNA segment into the vector. Synthetic linkers containing a variety of restriction sites are commercially available from a number of sources including International Biotechnologies, Inc., New Haven, Conn., and can be used to add additional restriction sites to a vector or DNA segment of this invention. Instructions for their use can be obtained from the supplier. Polynucleotide sequences, including the removable fragments and/or the linking sequences may also be prepared by direct synthesis techniques.

Also contemplated by the present invention are RNA equivalents of the above described recombinant DNA molecules.

The nucleic acids are combined with linear DNA molecules in an admixture thereof and a ligase can be added to effect ligation of the components. Any ligase available commercially is contemplated to perform the ligation reaction effectively using methods and conditions well known to those skilled in the art. A preferred ligase is T4 DNA ligase.

Volume exclusion agents may also be used to accelerate the ligation reaction. However, such agents may cause excessive intramolecular circularizations in some cases.

The recombinant DNA molecules or vectors of the present invention are introduced into host cells, via a procedure commonly known as transformation or transfection. The host cell can be either procaryotic or eukaryotic. Bacterial cells are preferred procaryotic host cells and typically are a strain of *E. coli* such as, for example, the MC1061 or JM109 strains. Preferred eukaryotic host cells include yeast and mammalian cells, preferably vertebrate cells such as those from a mouse, rat, monkey or human fibroblastic cell line. Preferred eukaryotic host cells include Chinese hamster ovary (CHO) cells available from the ATCC as CCL61 and NIH Swiss mouse embryo cells NIH/3T3 available from the ATCC as CRL 1658. One preferred means of effecting transformation is electroporation.

Transformation of appropriate host cells with a recombinant DNA molecule of the present invention is accomplished by well known methods that typically depend on the type of vector used. With regard to transformation of procaryotic host cells, see, for example, Cohen et al., *Proc. Natl. Acad. Sci. USA,* 69:2110 (1972); and Maniatis et al., *Molecular Cloning, A Laboratory Manual,* Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.,* 4:1730–37 (1984); Graham et al., *Virol.,* 52:456 (1973); and Wigler et al., *Proc. Natl. Acad. Sci. USA,* 76:1373–76 (1979).

Successfully transformed cells, i.e., cells that contain a recombinant DNA (rDNA) molecule of the present invention, are usually monitored by an appropriate immunological or functional assay. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.,* 98:503 (1975) or Berent et al., *Biotech.,* 3:208 (1985).

In addition to directly assaying for the presence of rDNA, successful transformation can be confirmed by well known immunological methods when the rDNA is capable of directing the expression of a subject polypeptide. For example, cells successfully transformed with a subject rDNA containing an expression vector produce a polypeptide displaying a characteristic antigenicity. Samples of a culture containing cells suspected of being transformed are harvested and assayed for a subject polypeptide using antibodies specific for that polypeptide antigen, such as those produced by an appropriate hybridoma.

Thus, in addition to the transformed host cells themselves, cultures of the cells are contemplated as within the present invention. The cultures include monoclonal (clonally homogeneous) cultures, or cultures derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

E. Eukaryotic Gene Regulation Systems

In another embodiment, the present invention contemplates an eukaryotic gene regulation system that comprises two different rDNA species, a rDNA for expressing a nucleus-targeted inducible repressor polypeptide and a rDNA containing an operator-regulated gene expression DNA segment. In a eukaryotic gene regulation system, the inducible repressor polypeptide specifically binds to the operator according to the teachings of this invention.

The system can be in the form of a container containing in separate packages, two different rDNA species, a first rDNA that encodes a nucleus-targeted inducible repressor polypeptide of this invention and a second rDNA that contains an operator-regulated gene expression DNA segment as described herein. In this form, the system provides the reagents for studies of in vitro regulation of gene expression, for preparing an in vitro system for regulation of eukaryotic gene expression, and for preparing transgenic mammals for in vivo regulation of gene expression.

An in vitro system for regulation of gene expression can take the form of a tissue culture system in which a eukaryotic cell line is stably transformed with the two above rDNA species, and preferably the second rDNA species contains a DNA segment that encodes a reporter polypeptide. In the cell line, the rDNA encoding a nucleus-targeted inducible repressor protein expresses a fusion protein of this invention under cell culturing conditions to produce a cell containing the expressed fusion protein. Thus, the invention contemplates a eukaryotic cell comprising at least one lac operator-containing nucleic acid segment operatively linked to a promoter-containing nucleic acid segment and a fusion protein comprising a nuclear transport signal amino acid residue sequence capable of binding to the lac operator. Such a cell line can be used for in vitro mutagenicity testing, whereby mutagenesis of the operator or the repressor by a mutagen can switch on expression of the reporter gene.

An eukaryotic gene regulation system can also take the form of a transgenic mammal.

Preparation of cell lines stably transfected with one or both of the rDNA's of an eukaryotic gene regulation system of this invention can be prepared by well known methods, such as described in the Examples herein below.

In another embodiment a eukaryotic gene regulation system can take the form of a tissue containing the above two rDNA's of this invention.

Tissues containing the two rDNA's that comprise a eukaryotic gene regulation system of the present invention may be prepared by introducing a recombinant nucleic acid molecule into a tissue, such as bone marrow, brain and liver, using known transformation techniques. These transformation techniques include transfection and infection by retroviruses carrying either a marker gene or a drug resistance gene. See for example, *Current Protocols in Molecular Biology,* Ausubel et al., eds., *John Wiley and Sons,* New York (1987) and Friedmann, T., *Science,* 244:1275–1281

(1989). A tissue containing a eukaryotic gene regulation system of the present invention may then be reintroduced into an animal using reconstitution techniques. See for example, Dick et al., *Cell*, 42:71 (1985).

A tissue containing a recombinant nucleic acid molecule of the present invention may also be prepared by introducing the two rDNA species described above into the germ line of a mammal. After introduction into the germ line the rDNA's are present in all the tissues of that mammal. See for example, Palmiter, et al., *Ann. Rev. Genet.*, 20:465–499 (1986).

Isolation of tissues from an animal whose tissues contain the two different rDNA species is accomplished using standard techniques. For example, the liver, lungs, spleen, or bone marrow can be removed using standard surgical techniques.

A tissue containing a eukaryotic gene regulation system of the present invention may also be produced by directly introducing the vectors containing the two different rDNA's into the animal. Direct vector delivery in vivo may be accomplished by transducing the desired cells and tissues with viral vectors or other physical gene transfer vehicles in vivo. Other physical agents including naked plasmids, cloned genes encapsulated in targetable liposomes or in erythrocyte ghosts have been use to introduce genes, proteins, toxins and other agents directly into whole animals. See, for example, the liposome-mediated gene delivery in vivo and expression of preproinsulin genes in recipient rats described by Nikolau, et al., *Proc. Natl. Acad. Sci., USA*, 80:1068 (1983) and Soriano, et al., *Proc. Natl. Acad. Sci., USA*, 80:7128 (1983). Direct injection of naked calcium phosphate-precipitated plasmid into rat liver and rat spleen or a protein-coated plasmid into the portal vein has resulted in gene expression of the foreign gene in the rat livers. See for example, Kaneda, et al., *Science*, 243:375 (1989).

In one embodiment, the invention contemplates a system for regulation of gene expression formulated for the convenience of the investigator of in vivo regulation of gene expression. In this embodiment, a first component of the system is a rDNA containing an operator-regulated gene expression DNA segment having convenient restriction endonuclease sites located in a region of the rDNA such that a preselected reporter gene can be inserted into the rDNA at one or more of the convenient restriction endonuclease sites. Expression of the inserted reporter gene is under the control of the operator-regulated gene expression DNA segment. Thus the investigator can produce an rDNA capable of expressing a preselected reporter gene that includes the operator controls according to a eukaryotic gene regulation system of this invention. The first component is then used to produce a transgenic mammal according to disclosures herein that has the rDNA of the first component with a preselected reporter gene under the operator controls of the first component.

A second component of the system in this embodiment is a transgenic mammal containing a rDNA that encodes a nucleus-targeted inducible repressor polypeptide. The second (transgenic mammal) component is used to cross with the transgenic animal produced with the rDNA of the first component to produce a progeny transgenic mammal having both the rDNA of the first component and the rDNA present in the second component to form a complete eukaryotic gene regulation system. Thus this embodiment allows an investigator to "tailor-make" an eukaryotic gene regulation system having a reporter gene of his choice under the regulation of the operator.

Crossing of transgenic mammals to produce a progeny transgenic mammal containing the transgene of each parent transgenic mammal is a well known procedure in mammalian genetics. The procedure generally involves mating male and female transgenic mammals (founders) to produce offspring, at least some of which will be transgenic mammals containing the transgenes of both parents, i.e., a hybrid transgenic mammal. The presence in the offspring of the desired rDNA transgenes derived from each founding parent can be verified by the same methods as described for the preparation of a transgenic mammal. Offspring transgenic mammals are thereby produced having rDNAs from each founder parent that together comprise a eukaryotic gene regulation system of the present invention.

The first component is typically provided in the form of a package containing a rDNA of the first component, together with instructions for using the rDNA molecule.

F. Transgenic Organisms

The present invention has application in the genetic transformation of multicellular eukaryotic organisms which undergo syngamy, i.e., sexual reproduction by union of gamete cells. Preferred organisms include mammals, birds, fish, gymnosperms and angiosperms.

Thus, the present invention contemplates a non-human mammal containing a rDNA of the present invention in the genome of the mammal's somatic and germ cells, i.e., a transgenic mammal. Mammals containing a rDNA of the present invention are typically prepared using the standard transgenic technology described in Hogan et al., *Manipulating the Mouse Embryo: A Laboratory Manual*, Cold Spring Harbor, N.Y. (1987); and Palmiter et al., *Ann. Rev. Genet.*, 20:465–499 (1986); which methods are described further herein. Production of transgenic mammals is also possible using the homologous recombination transgenic systems described by Capecchi, *Science*, 244:288–292 (1989). Preparation of transgenic mammals has also been described in U.S. Pat. Nos. 4,736,866, 4,870,009, 4,873,191 and 4,873,316.

One technique for transgenically altering a mammal is to microinject a rDNA into the male pronucleus of the fertilized mammalian egg to cause one or more copies of the rDNA to be retained in the cells of the developing mammal. The rDNA of interest is isolated in a linear form with most of the sequences used for replication in bacteria removed. Linearization and removal of excess vector sequences results in a greater efficiency in production of transgenic mammals. See for example, Brinster, et al., *Proc. Natl. Acad. Sci., USA*, 82:4438–4442 (1985). Usually up to 40 percent of the mammals developing from the injected eggs contain at least 1 copy of the rDNA in their tissues. These transgenic mammals usually transmit the gene through the germ line to the next generation. The progeny of the transgenically manipulated embryos may be tested for the presence of the construct by Southern blot analysis of a segment of tissue. Typically, a small part of the tail is used for this purpose. The stable integration of the rDNA into the genome of the transgenic embryos allows permanent transgenic mammal lines carrying the rDNA to be established.

Alternative methods for producing a non-human mammal containing a rDNA of the present invention include infection of fertilized eggs, embryo-derived stem cells, totipotent embryonal carcinoma (Ec) cells, or early cleavage embryos with viral expression vectors containing the rDNA. See for example, Palmiter et al., *Ann. Rev. Genet.*, 20:465–499 (1986) and Capecchi, *Science*, 244:1288–1292 (1989).

In one embodiment, a transgenic non-human mammal contains a rDNA of this invention capable of expressing a nucleus-targeted inducible repressor polypeptide. In preferred embodiments, the rDNA encodes a fusion protein comprising a lac repressor polypeptide segment operatively linked to a nuclear transport signal coding segment. A particularly preferred transgenic mammal contains a fusion protein encoded by the rDNA pPy5'SSA1 or pPy(SL)SS1A.

In another embodiment, a transgenic mammal contains a rDNA of this invention capable of expressing a operator-regulated reporter polypeptide. In preferred embodiments, the rDNA encodes a reporter protein under the control of at least one lac operator. In a related embodiment, the rDNA encodes a reporter gene that is toxic to the cell in which it is expressed, such that, upon induction, the cells in which the repressor is induced are killed or otherwise toxically affected. This latter embodiment is particularly useful for studying the effect of the loss of the affected cell type upon induction in the transgenic animal at preselected times during various stages of the animal's development.

In a further embodiment, a transgenic mammal is contemplated that contains both rDNA species described above for a eukaryotic gene regulation system of this invention.

A transgenic mammal can be any species of mammal, including agriculturally significant species, such as sheep, cow, lamb, horse and the like. Preferred are animals significant for scientific purposes, including but not limited to rabbits, primates and rodents, such as mice, rats and the like. A transgenic mammal is not human.

Exemplary preparation of a transgenic mouse is described in the Examples.

In another embodiment the invention contemplates a transgenic mammal of this invention having an inducer of this invention present in a body fluid sample, tissue section or other sample isolated from the transgenic animal. The inducer present depends on the repressor polypeptide encoded in the transgenic animal's rDNA, and is an inducer for inducing that repressor. Thus, for a transgenic mammal containing an rDNA that encodes a lac repressor-derived polypeptide, the inducer present in the mammal is an inducer of lac repressor, namely a galactoside, a thiogalactoside or derivative thereof.

A transgenic mammal of this invention can contain a lac repressor inducer at blood (plasma) concentrations of at least about 10 picomolar (pM) equivalents of IPTG when measured in a standard induction assay. Preferably, the transgenic animal contains at least 1 micromolar (uM) equivalents, and more preferably at least about 100 uM equivalents, of IPTG.

An IPTG equivalent is an amount of inducer that produces the same amount of induction of lac repressor in a standard induction assay as a predetermined amount of IPTG, based on a dose-induction response curve using IPTG as a control for induction. A preferred standard induction assay is the IPTG spot assay described in Example 1B.

Thus, in preferred embodiments a transgenic mammal having a rDNA that encodes a lac repressor-derived nucleus-targeted inducible repressor polypeptide further comprises a body sample concentration of inducer equal to at least about 10 picomolar equivalents of IPTG. Preferably, the inducer is a galactoside or thiogalactoside.

The amount of an inducer within a body fluid sample, tissue section or other sample isolated from an animal can be determined by chemical, immunological or biological assays. Preferred chemical analysis methods include nuclear magnetic resonance based detection, high pressure liquid chromatography, infrared spectrometry and the like. Preferred immunological detection methods include radio-immuno assay, enzyme-linked immuno absorbance assays and the like.

Preferred biological assays include the fluorescence dependent assay using fluorescein tagged substrates of β-galactosidase as has been described by Nolan et al., *Proc. Natl. Acad. Sci., USA*, 85:2603–2607 (1988) and commercially available from Molecular Probes, Inc., Eugene, Oreg., as the FluoReporter™ LacZ Flow Cytometry Kit. This procedure uses an ultra-pure fluorescein di-β-D-galactopyranoside (FDG) as a substrate for the lac Z-β-D-galactosidase gene to allow the florescent detection of induced galactosidase within a single cell when under the control of the lac operator. This system is used to detect the presence of an inducer within a body sample and is conducted by first lysing any cells present in the body sample to form a suspension sample containing inducer and then purifying the inducer in the sample using high pressure liquid chromatography or similar methods. The resulting purified sample is then applied to bacterial or mammalian cells having the lac operator controlling the expression of the Lac β-galactosidase gene, together with the fluorescein di-β-D-galactopyranoside as a substrate. The amount of specific fluorescence is measured thereby determining the amount of inducer that is present in the body sample that has derepressed the lac operator resulting in β-galactosidase production.

G. Methods of Genetically Programming a Cell within an Organism with A Eukaryotic Gene Regulation System The present invention also contemplates a method of introducing a eukaryotic gene regulation system into a cell, i.e., genetically programming a cell, within an organism by introducing the rDNA's of a eukaryotic gene regulation system of the present invention into the genome of a zygote to produce a genetically altered zygote or into the genome of individual somatic cells in the organism. The genetically altered zygote is then maintained under appropriate biological conditions for a time period equal to a gestation period or a substantial portion of a gestation period that is sufficient for the genetically altered zygote to develop into a transgenic organism containing at least 1 copy of the rDNA's of a eukaryotic gene regulation system of the present invention.

The term "genetically programming" as used herein means to permanently alter the DNA content of a cell within an organism such as a mammal so that a eukaryotic gene regulation system has been introduced into the genome of the cell of the organism. Thereafter, the administration of inducer to the cell can derepress the repressor protein causing the reporter gene to be expressed in the cell and thereby produce a biological effect. Typically, this genetic programming is accomplished by introducing the rDNA's of a eukaryotic gene regulation system of the present invention into the genome of the organism.

Any multicellular eukaryotic organism which undergoes sexual reproduction by the union of gamete cells may be genetically programmed using a rDNA of a eukaryotic gene regulation system of the present invention. Examples of such multicellular eukaryotic organisms include amphibians, reptiles, birds, mammals, bony fishes, cartilaginous fishes, cyclostomes, arthropods, insects, mollusks, thallaphytes, embryophytes including gymnosperms and angiosperms. In preferred embodiments, the multicellular eukaryotic organism is a mammal, bird, fish, gymnosperm or an angiosperm.

A transgenic organism is an organism that has been transformed by the introduction of a recombinant nucleic acid molecule into its genome. Typically, the recombinant nucleic acid molecule will be present in all of the germ cells and somatic cells of the transgenic organism. Examples of transgenic organisms include transgenic mammals, transgenic fish, transgenic mice, transgenic rats and transgenic plants including monocots and dicots. See for example, Gasser et al., *Science*, 244:1293–1299 (1989); European Patent Application No. 0257472 filed Aug. 13, 1987 by De La Pena et al.; PCT Pub. No. WO 88/02405 filed Oct. 1, 1987 by Trulson et al.; PCT Pub. No. WO 87/00551 filed Jul. 16, 1986 by Verma, and PCT Pub. No. WO 88/09374 filed May 20, 1988 by Topfer et al.

Methods for producing transgenic organisms containing a rDNA of the present invention include standard transgenic technology; infection of the zygote or organism by viruses including retroviruses; infection of a tissue with viruses and then reintroducing the tissue into an animal; and introduction of a rDNA into an embryonic stem cell of a mammal followed by appropriate manipulation of the embryonic stem cell to produce a transgenic animal. See for example, Wagner, et al., U.S. Pat. No. 4,873,191 (Oct. 10, 1989); Rogers, et al., *Meth. in Enzymol.*, 153:253–277 (1987); Verma et al., *PCT Publication No. WO*87/00551; Cocking et al., *Science*, 236:1259–1262 (1987); and Luskin et al., *Neuron* 1:635–647 (1988).

A cell within the organism that contains the rDNA's of an eukaryotic gene regulation system of the present invention is contacted with an inducer in an effective amount and for a time period sufficient for the inducer to be taken up by the cell and for the inducer to bind the repressor such that the repressor dissociates from the operator, and the reporter gene is expressed within that cell and thereby genetically program the cell of the organism.

Typically, the cell is contacted under biological growth conditions, appropriate for that organism for a sufficient time period. The biological growth conditions must allow the cell containing the rDNA's of a eukaryotic gene regulation system to express the gene encoding the nucleus-targeted inducible repressor polypeptide. This time period is typically of a length to allow the gene present in the rDNA that encodes the nucleus-targeted inducible repressor polypeptide to be expressed. During expression the gene is first transcribed into RNA by RNA polymerase and then the RNA is translated into protein to produce the nucleus-targeted inducible repressor polypeptide. The nucleus-targeted inducible repressor polypeptide then accumulates in the nucleus by means of the transport function provided by the nuclear transport signal coding sequence and binds to the operator containing DNA segment to repress the expression of the operator-regulated reporter gene.

Inducer is then administered to the transgenic animal by a variety of means to deliver the inducer to the cell (i.e., contact the cell) containing the eukaryotic gene regulation system to be induced, and depends in part on the cell type to be induced and tissue in which the cell is located in the organism. Administration can be topical, oral, as by ingestion, intravenous, intramuscular, intradermal or intraperitoneal, and can be accomplished by a single dose, by repeated doses, or by continuous infusion. A preferred means for continuous infusion is an implantable osmotic pump.

An effective amount of inducer is an amount sufficient to bind repressor and derepress the operator-regulated reporter gene, thereby causing expression of the reporter gene product in the contacted cell. Preferred amounts of inducer effective to bind repressor and derepress the regulated gene depend on degree and extent of derepression desired in the cell to be genetically programmed and regulated.

Typically, an effective amount of inducer to be contacted with a cell to be regulated is in the range of 10 picomolar (pM) to 500 millimolar (mM), preferably about 1 mM to 200 mM, and more preferably about 50 mM. Thus in one embodiment, inducer is administered to a transgenic organism, such as an animal, in an amount sufficient to produce a blood concentration having the above effective amount of inducer.

Transgenic mammals having at least 1 cell containing the rDNA's of a eukaryotic gene regulation system of the present invention can be produced using methods well known in the art. See for example, Wagner et al., U.S. Pat. No. 4,873,191 (Oct. 10, 1989); Hogan et al., Manipulating the Mouse Embryo: A Laboratory Manual, Cold Springs Harbor, N.Y. (1987); Capecchi, *Science*, 244:288–292 (1989); and Luskin et al., *Neuron* 1:635–647 (1988).

In preferred embodiments the transgenic mammal of the present invention is produced by:

1) microinjecting a rDNA into a fertilized mammalian egg to produce a genetically altered mammalian egg;

2) implanting the genetically altered mammalian egg into a host female mammal;

3) maintaining the host female mammal for a time period equal to a substantial portion of a gestation period of said mammal.

4) harvesting a transgenic mammal having at least one cell containing a rDNA that has developed from the genetically altered mammalian egg.

A rDNA of the present invention is provided, typically in linearized form, by linearizing the rDNA with at least 1 restriction endonuclease. In addition, the rDNA containing the genes for a eukaryotic gene regulation system may be isolated from the vector sequences using 1 or more restriction endonucleases. Techniques for manipulating and linearizing recombinant nucleic acid molecules are well known and include the techniques described in *Molecular Cloning: A Laboratory Manual, Second Edition,* Maniatis et al., eds., Cold Spring Harbor, N.Y. (1989).

A fertilized mammalian egg may be obtained from a suitable female mammal by inducing superovulation with gonadotropins. Typically, pregnant mare's serum is used to mimic the follicle-stimulating hormone (FSH) in combination with human chorionic gonadotropin (hCG) to mimic luteinizing hormone (LH). The efficient induction of superovulation in mice depends as is well known on several variables including the age and weight of the females, the dose and timing of the gonadotropin administration, and the particular strain of mice used. In addition, the number of superovulated eggs that become fertilized depends on the reproductive performance of the stud males. See, for example, *Manipulating the Embryo: A Laboratory Manual,* Hogan et al., eds., Cold Spring Harbor, N.Y. (1986).

The linearized rDNA may be microinjected into the mammalian egg to produce a genetically altered mammalian egg using well known techniques. Typically, the linearized rDNA is microinjected directly into the pronuclei of the fertilized mouse eggs as has been described by Gordon et al., *Proc. Natl. Acad. Sci., USA,* 77:7380–7384 (1980). This leads to the stable chromosomal integration of the rDNA in approximately 10 to 40 percent of the surviving embryos. See for example, Brinster et al., *Proc. Natl. Acad. Sci., USA,*

82:4438–4442 (1985). In most cases, the integration appears to occur at the 1 cell stage, as a result the rDNA is present in every cell of the transgenic animal, including all of the primordial germ cells. The number of copies of the foreign rDNA that are retained in each cell can range from 1 to several hundred and does not appear to depend on the number of rDNA injected into the egg as is well known.

An alternative method for introducing genes into the mouse germ line is the infection of embryos with virus vectors. The embryos can infected by either wild-type or recombinant viruses leading to the stable of integration of viral genomes into the host chromosomes. See, for example, Jaenisch et al., *Cell*, 24:519–529 (1981). One particularly useful class of viral vectors are virus vector derived from retroviruses. Retroviral integration occurs through a precise mechanism, leading to the insertion of single copies of the virus on the host chromosome. The frequency of obtaining transgenic animals by retroviral infection of embryos can be as high as that obtained by microinjection of the rDNA and appears to depend greatly on the titre of virus used. See, for example, van der Putten et al., *Proc. Natl. Acad. Sci., USA*, 82:6148–6152 (1985).

Another method of transferring new genetic information into the mouse embryo involves the introduction of the rDNA into embryonic stem cells and then introducing the embryonic stem cells into the embryo. The embryonic stem cells can be derived from normal blastocysts and these cells have been shown to colonize the germ line regularly and the somatic tissues when introduced into the embryo. See, for example, Bradley et al., *Nature*, 309:255–256 (1984). Typically, the embryo-derived stem cells are transfected with the rDNA and the embryo-derived stem cells further cultured for a time period sufficient to allow the rDNA to integrate into the genome of the cell. In some situations this integration may occur by homologous recombination with a gene that is present in the genome of the embryo-derived stem cell. See, for example, Capecchi, *Science*, 244:1288–1292 (1989). The embryo stem cells that have incorporated the rDNA into their genome may be selected and used to produce a purified genetically altered embryo derived stem cell population. See, for example, Mansour et al., *Nature*, 336:348 (1988). The embryo derived stem cell is then injected into the blastocoel cavity of a preimplantation mouse embryo and the blastocyst is surgically transferred to the uterus of a foster mother where development is allowed to progress to term. The resulting animal is chimeric in that it is composed from cells derived of both the donor embryo derived stem cells and the host blastocyst. Heterozygous siblings are interbred to produce animals that are homozygous for the rDNA. See for example, Capecchi, *Science*, 244:1288–1292 (1989).

The genetically altered mammalian egg is implanted into host female mammals. Methods for implanting genetically altered mammalian eggs into host females are well known. See, for example, Hogan et al., *Manipulating the Mouse Embryo: A Laboratory Manual*, Cold Spring Harbor Laboratory, Cold Spring Harbor, N.Y. (1986). Pseudopregnant recipient females may be produced by mating females in natural estrus with vasectomized or genetically sterile males. After mating with a sterile male, the female reproduction tract becomes receptive for transferred embryos even though her own unfertilized eggs degenerate. The genetically altered mammalian eggs are then transferred to the ampullae or the uterine horns of the pseudopregnant recipient. If the genetically altered mammalian egg is transferred into the ampullae it must be enclosed in a zona pellucida membrane. If it is transferred into the uterine horns the genetically altered mammalian egg does not require a zona pellucida membrane.

The host female mammals containing the implanted genetically altered mammalian eggs are maintained for a sufficient time period to give birth to a transgenic mammal having at least 1 cell containing a rDNA of the present invention that has developed from the genetically altered mammalian egg. Typically this gestation period is between 19 to 20 days depending on the particular mouse strain. The breeding and care of mice is well known. See for example, *Manipulating the Mouse Embryo: A Laboratory Manual*, Hogan et al., eds., Cold Spring Harbor, N.Y., (1986).

In other preferred embodiments, the transgenic animal of the present invention is produced by infecting an animal with a vector containing a selectable marker gene and one or both of the rDNA's of a eukaryotic gene regulation system to produce a genetically altered animal cell.

A marker gene is a gene that codes for a protein that can be detected when expressed in a particular cell or cell type. Typical marker genes include beta galactosidase or luciferase. Use of a beta galactosidase marker gene has been described by Luskin et al., *Neuron*, 1:635–647 (1988).

The infection of cells within an animal using a replication incompetent retroviral vector has been described by Luskin et al., *Neuron*, 1:635–647 (1988).

In one embodiment, an animal that contains a eukaryotic gene regulation system in specific tissues or cells can be used to test a material, composition, or compound suspected of being a carcinogen. The animal is exposed to the particular material or compound and the mutagenic effect on the animal is determined by the derepression of the operator-regulated reporter gene segment as an indication of the carcinogenicity of the compound or material. The specific effects determined and observed in the animal depend upon the reporter gene expressed and its effect on the cells in which the reporter gene is expressed.

The composition suspected of having carcinogenic activity is introduced into the animal by any suitable method including injection, or ingestion or topical administration.

The animal is then maintained for a predetermined time period that is sufficient to allow the composition to produce a mutagenic effect on the genes of the eukaryotic gene regulation system. Typically, this time period ranges from several minutes to several days depending on the time the composition requires to mutagenize the genes.

The physiological process or parameter assayed as an indication of mutagenesis depends upon the particular physiological alteration produced by the expression of the reporter gene.

A change in a physiologic parameter is determined by measuring that parameter before introduction of the composition into the animal and comparing that measured value to a measured value determined in identical manner after introduction of the composition into the animal.

The level of expression of the reporter gene product in the transgenic animals may alter the sensitivity of transgenic mice to the effects of the suspected carcinogen. Therefore, selection of transgenic mice with varying transgene copy numbers of the reporter gene will alter the sensitivity of the transgenic mice to the suspected carcinogen. For example, if a higher level of reporter gene product creates a more substantial change in the measured physiological parameter in response to a particular carcinogen, transgenic mice with a higher transgenic copy number would be particularly useful as a carcinogen detection system.

H. Inducers

An inducer is a molecule, typically a low molecular weight molecule, that binds to an inducible repressor polypeptide of this invention and causes the repressor to dissociate from a nucleic acid operator sequence to which it is bound. The prototype lac repressor is induced by a class of galactoside derivatives and are exemplary of inducers for the present invention. See, for example Miller, J. H., in "The Operon", p. 31–88, 34, Miller et al., eds., Cold Spring Harbor Laboratory, New York, 1980; and Jacob et al., *J. Mol. Biol.*, 3:318–356, 324 (1961).

In one embodiment, lac repressor inducers of the present invention are derivatives of galactoside that are modified to increase the half-life of the derivative in physiological solutions. Preferred modified galactosides are thiogalactoside derivatives such as the prototype isopropyl-beta-D-thiogalactoside (IPTG).

Preferred modified thiogalactosides have the general formula R-beta-D-thiogalactoside, where R can be: an alkyl group with a terminal nucleophile such as an amino group; an alkyl group with a terminal electrophile such as N-hydroxysuccinimide, isothiocyanate, phosphonate or maleimide; an alkyl group; a branched alkyl group; a branched alkyl group with anelectrophile; a branched alkyl group with a nucleophile; an alkene; an alkene with a terminal nucleophile; an alkyne; an alkyne with a terminal nucleophile; an ester; an ester containing N-hydroxysuccinimide, an alkyl or paranitrophenoxy; a terminal alcohol such as methanol, ethanol, 1-propanol, 1-butanol, 1-pentanol and the like; a protein; a cellular receptor binding protein; polyethylene glycol; a carboxyl group; at least one atom bonded to a sulfur atom; or an acid labile group that is labile at a pH of less than 5.0.

In preferred embodiments where R is a protein or a cellular receptor binding protein, any protein such as albumin, bovine serum albumin and the like is contemplated. Useful cellular receptor binding proteins include low density lipoprotein (LDL), LDL containing a nuclear transport signal and the like.

Preferred modified thiogalactosides have the general formula R-beta-D-thiogalactoside, where R can be cyclohexyl, 2-[1,3-diamino] propyl, 4-amino-1-butyl, 3-amino-1-propyl, 3-carbosyl-1-propyl, 3-phosphato-1-propyl, methyl (MTG), ethyl (ETG), isopropyl, isobutyl, n-propyl (NPG), n-butyl (NBG), n-pentyl, 2-nitrilo-ethyl, and the like, and can be sodium. R cannot be phenyl, or alkyl-phenyl derivatives.

The R group can be used to crosslink the modified thiogalactoside to a carrier molecule or to a molecule that targets the modified thiogalactoside to a specific preselected tissue. Typical linking groups for crosslinking are well known in the arts. R groups that present a terminal amino or diamino groups are preferred to provide a modified thiogalactoside with the capability to be crosslinked. Other preferred crosslinking groups include nucteophiles such as thiols or amino groups, or electrophiles such as N-hydroxysuccinimide, isothiocynate, phosphonate or maleimide.

An important and unexpected aspect of the invention is the discovery that modified thiogalactosides are selectively taken up in specific tissues of all animal as described in Example 5. The tissue specificity of uptake depends on the structure of the R group, and to a lesser degree on the route of delivery of the inducer to the cell or tissue. Thus, by preselecting an R group on a modified thiogalactoside of this invention, one can direct the uptake, and therefore the induction, to specific tissues or cell types. This feature of the inducer is particularly useful when inducing cells in whole animals such as transgenic animals containing a eukaryotic gene regulation system as described herein. Tissue specific inducers provide an important and simple method of controlling the tissue for induction, and can supplement the tissue specificity of a eukaryotic gene regulation system that utilizes a tissue specific promoter for expressing the reporter polypeptide.

The β-D-thiogalactoside derivatives of this invention are prepared using conventional procedures [Schmidt, et al. *Liebigs Ann. Chem.*, 1249 (1983). Briefly, 2,3,4,6 tetra-O-acetyl-D-galactose is obtained from the penta-O-acetylgalactose as described for the penta-O-acetylglucose [*Organikum*, 13. Aufl., S. 452, VEB Deutscher Verlag der Wissenschaften, Berlin 1974]. The tetra-O-acetyl-D-galactose is reacted with trichloro acetonitrile in the presence of NAH base to give the 1-O-trichloracetimidate, primarily in the β configuration. The acetimidate is reacted with the appropriate alkylthiol (RSH), catalyzed by BF₃-diethylether adduct, to give the β-alkylgalactoside, which is deblocked using sodium methoxide.

The alkylthiols used to prepare the corresponding modified thiogalactosides are methanethiol for MTG, ethanethiol for ETG, isopropanethiol for IPTG, n-propanethiol for NPG, n-butanethiol for NBG, etc., for each modified thiogalactoside.

Methods for preparing pharmaceutical compositions which contain a galactoside, thiogalactoside or modified thiogalactoside as described herein as an active ingredient is well understood in the art. Typically, such compositions are prepared as injectables, either as liquid solutions or suspensions, however, solid forms suitable for solution in, or suspension in, liquid prior to injection can also be prepared. The preparation can also be emulsified. The active physiologic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

Some modified galactosides can be formulated into the composition as neutralized pharmaceutically acceptable salt forms. Where free amino groups are present, pharmaceutically acceptable salts include acid addition salts which are formed with inorganic acids such as, for example, hydrochloric or phosphoric acids, or such organic acids as acetic, oxalic, tartaric, mandelic, and the like. When free carboxyl groups are present, salts can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical galactoside-containing compositions can be conventionally administered intravenously, as by injection of a unit dose, for example. The term "unit dose" when used in reference to a pharmaceutical composition of the present invention refers to physically discrete units suitable as unitary dosage for transgenic mammals, each unit containing a predetermined quantity of active material calculated to produce the desired physiologic effect in association with the required diluent; i.e., carrier, or vehicle.

The compositions are administered in a manner compatible with the dosage formulation, and in a physiologically effective amount. The quantity to be administered depends on the subject to be treated, and capacity of the subject's genetic system to utilize the active ingredient. Precise amounts of active ingredient required to be administered depend on the judgment of the practitioner and are peculiar to each type of transgenic mammal. However, suitable dosage ranges for systemic application are of the order of 0.01 to 10, preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous infusion sufficient to maintain concentrations of ten nanomolar to ten micromolar in the blood are contemplated.

In preferred embodiments, the biologically active galactoside is encapsulated in a protective coating. The encapsulation material can be a membrane, a gel, a polymer or the like. The encapsulation material functions to protect the material it contains and to control the flow of the material in and out of the encapsulation device. Typical of such devices is an osmotic pump. See, Theeuwes, *J. Pharm. Sci.,* 64:1987 (1975); and U.S. Pat. No. 4,971,790.

Thus, the present invention provides a nonirritating pharmaceutical composition for subdermal administration, designed to release effective amounts of a lac operon inducing galactoside over a predetermined period of time. The composition includes an encapsulating polymer, such as poly(ε-caprolactone) or a copolymer of ε-caprolactone with other lactones as described in U.S. Pat. No. 4,148,871, a polyactide as described in U.S. Pat. No. 3,887,699, and the like. The galactoside may be either intimately mixed with the polymer composition, or contained within the cavity of a hollow device constructed from the polymer. The shape of these polymeric devices may be a cylinder, sphere, slab, or any other common geometric form. When the drug is intimately mixed with the polymer or copolymer, the proportion of the drug may range from 0.01% by weight of drug and 99.9% by weight of polymer or copolymer to 90% by weight of drug and 10% by weight of polymer or copolymer. When the drug is contained within the cavity of the polymer device, it may be present as a solid, preferably micronized, powder or mixed with a suitable solvent, diluent, or dispersing agent. When the invention is applied subdermally, using either minor surgery or trocar injection, it has the property of releasing pre-determined amounts of the drug or drugs over a predetermined period of time.

The polymer-galactoside composite, when implanted subdermally, provides a convenient formulation for controlled galactoside administration which requires no attention on the part of the user and is capable of delivering the drug at physiologically effective levels for periods of up to at least one year.

The preparation of formulations in which the drug is contained within the cavity of the polymeric device of the present invention is a two step process. The first step involves preparation of the drug-free polymeric device. This is accomplished by conventional methods, such as compression molding, melt coating, annealing rolled films, or extrusion. The drug may be introduced into the cavity of such devices as a micronized powder, or as a mixture with a suitable solvent, diluent or dispersing agent. It is desirable that the amount of drug present be such that at least some of it is retained in the solid form. As is known to those skilled in the art, this will have the effect of producing a constant rate of release of the galactoside from the polymer device. The nature of the solvent, diluent or dispersing agent should be such that it does not dissolve the polymer to any appreciable extent, but that the rate of diffusion of the galactoside through it be very rapid compared with diffusion through the polymer. Examples of suitable solvents, diluents, and dispersing agents include sesame oil, mineral oil, various commercial preparations such as carboxymethyl cellulose sorbitan trioleate, and sorbitan stearate, as well as low molecular weight polymers or oligomers including polyethers and polyesters.

As is well documented in the literature, and as well known to those skilled in the art, the amount of drug, the dimensions of the polymeric device, and the amount of diluent, solvent or dispersing agent, may be varied such that the rate of the drug delivery and the time over which the drug is delivered are considered optimum for the particular therapeutic application.

The lac operon-inducing galactoside can also be conveniently administered to the transgenic animal through the animal's diet. For example, the galactoside can be administered through the animal's water supply by limiting the source of dietary water for a predetermined time to that which contains an effective amount of galactoside, such as about 0.25M to about 0.75M, and preferably about 0.5M, galactoside. A dietary water dispensing device, such as a water bottle, tray or container from which the transgenic animal can drink is provided with the water therein containing a galactoside as described herein.

EXAMPLES

The following description provides details of the manner in which the embodiments of the present invention may be made and used in order to achieve the rapid recovery and examination of test genes from transgenic animals. This description, while exemplary of the present invention, is not to be construed as specifically limiting the invention. Variations and equivalents, now known or later developed, which would be within the understanding and technical competence of one skilled in this art are to be considered as falling within the scope of this invention, which is limited only as set forth by the appended claims.

1. Preparation of rDNA Molecule Coding for a Nucleus-Targeted Inducible Repressor Polypeptide A. Inducible Repressor-Coding rDNA The inducible repressor-coding rDNA designated pI$^q$Py1A was deposited on Jan. 10, 1991 with the American Type Culture Collection (ATCC) under the Budapest Treaty (ATCC, Rockville, Md.) and has been assigned ATCC #_____. The pIqPy1A plasmid contains the following sequence elements: genes encoding ampicillin resistance (Amp$^r$), origin of replication (oriC), and single stranded phage replication origin (f1); Lac I$^q$ gene from pMJR1560 [Stark, N., *Gene,* 51:255–267 (1987)] where the upstream ATGs have been removed and the GTG initiator codon has been replaced with the Kozak consensus sequence [Kozak, M., *Cell,* 44:283–292 (1986)]; genes encoding SV40 small intron and poly A addition signal from pMC1-neo [Thomas et al., *Cell,* 51:503–512 (1987)]; genes encoding a thymidine kinase promoter driving hygromycin resistance gene from Cos-203 [Kioussis et al., *EMBO J.,* 6:355–361 (1987)]; hygromycin resistance gene from Cos-203 (Kioussis et al., supra); and a gene encoding a thymidine kinase poly A addition site from Cos-203 (Kioussis et al., supra). The promoter, Lac I gene segment, SV40 intron and polyadenylation signal are shown schematically in FIG. 1.

B. Nuclear Transport Signal-Coding Nucleic Acid Segment

The inducible repressor-coding rDNA prepared above was modified to include a nucleic acid segment coding for the nuclear transport signal from the SV40 Large T antigen that has been previously described by Lanford et al., *Cell*, 46:575 (1986). This nuclear transport signal comprises a 7 amino acid peptide fragment, Pro-Lys-Lys-Lys-Arg-Lys-Val, (SEQ ID NO1) located at amino acid residue position numbers 126 through 132 in the Large T antigen of SV40.

The nucleic acid segment coding for the nuclear transport signal was operatively inserted into the rDNA molecule coding for the inducible repressor using site directed mutagenesis performed using the mutagene site-directed mutagenesis kit (Biorad Laboratories, Richmond, Calif.) and Biorad's instructions provided with that kit together with the procedures and some materials provided in the p Bluescript®II phagemid kit (Stratagene). Briefly, the uracil-containing single-stranded template required for the site-directed mutagenesis procedure was prepared first by maintaining a 5 ml culture of XL1-blue cells (Stratagene) containing the pI$^q$Py1A plasmid at 37C. for 3 hours. One ul of a solution containing 1×10$^{11}$ plaque forming units (pfu) per ml of VCS-M13 helper phage (Stratagene) was then added to the 5 ml culture and the culture was further maintained at 37C. for 3 hours. During this time, single-stranded M13 phage containing the single-stranded pI$^q$Py1A DNA are formed and released from the XL1-blue bacteria.

The bacteria in this culture were killed by heating the culture to 68C. for 15 minutes. The killed bacteria were removed from culture, by centrifuging the culture at 10,000×g to produce a supernatant containing the pI$^q$Py1A single-stranded phage. One ml of this supernatant was added to a previously established 5 ml culture of CJ236 bacteria (Biorad Laboratories, Richmond, Calif.) that was in the late log phase of growth. The culture was maintained at 37C. for 10 min. and then 10 ul of the culture was plated onto LB bacterial plates (LB media contains 10 g/L of bactotryptone, 5 g/L of yeast extract, 5 g/L of NaCL containing both 50 ug/ml of ampicillin and 30 ug/ml of chloramphenicol. The resulting bacterial plates were maintained at 37C. for 12–18 hours to allow individual colonies of CJ236 bacteria containing the pI$^q$Py1A single-stranded M13 phage to form.

One of the resulting colonies was selected and used to initiate a 5 ml bacterial culture in superbroth media consisting of 35 g/L bactotryptone, 20 g/l yeast extract, 5 g/L sodium chloride at pH 7.5. This 5 ml culture was maintained at 37C. for 6 hours and then transferred to 150 mls of superbroth in a 250 ml flask and further maintained at 37C. for one hour with constant shaking. Then 100 ul of a solution containing 1×10$^{11}$ PFU/ml of VCS-M13 helper phage (Stratagene) was added to the culture and the culture was maintained at 37C. for 12–18 hours with constant shaking. During this time, a culture of CJ236 bacteria containing the pI$^q$Py1A single-stranded DNA template was produced.

This culture was then used to isolate the pI$^q$Py1A single-stranded template using the single-stranded phage DNA isolation procedures described in the p Bluescript® II manual (Stratagene). Briefly, 50 μl of the culture containing pI$^q$Py1A single-stranded phage produced above was centrifuged at 17,000×g to produce a clarified supernatant. Approximately 1.2 ml of this supernatant was transferred to an eppendorf centrifuge tube and 300 ul of a solution containing 3.5M Ammonium Acetate at PH 7.5 and 20% polyethylene glycol (PEG) was admixed to it. The resulting admixture was maintained at 25C. for 15 minutes. The admixture was centrifuged at 11,000×g for 20 minutes to pellet the single-stranded phage present. The resulting supernatant was removed from the phage pellet.

The phage pellet was resuspended in 300 μl of TE buffer consisting of 10 mm Tris-HCl at pH 8.0 and 1 mm EDTA. The resulting solution was admixed with an equal volume of phenol/chloroform and the resulting aqueous phase transferred to a fresh tube. The aqueous phase was reextracted with phenol/chloroform until no significant interface between the organic and aqueous phase was observed. The aqueous phase was then admixed with an equal volume of chloroform and the single-stranded DNA isolated from the aqueous phase by ethanol precipitation using Ammonium Acetate.

The amount of single-stranded pI$^q$Py1A DNA isolated was determined by gel electrophoresis. This single-stranded pI$^q$Py1A DNA was then used as a template in the site-directed mutagenesis procedure below.

The nucleic acid segment coding for the nuclear transport signal was then inserted into the inducible repressor-coding DNA sequence using the pI$^q$Py1A single-stranded DNA template prepared above and the polynucleotides listed in Table I in the site directed mutagenesis protocol described in the manufacturer's instructions provided with the Mutator™ site-directed Mutagenesis Kit (Stratagene). The nucleic acid segment coding for the SV40 nuclear transport signal was placed at two different locations within the pI$^q$Py1A template DNA. TAG polynucleotide P1 (Table I) was used to place the nuclear transport signal at nucleotide +4 with respect to two adenine nucleotides within the start codon of the LacI gene present in the pI$^q$Py1A template. This construct has been designated pPy5'SS1A as shown in FIG. 1. In a separate construct TAG polynucleotide P2 (Table I) was used to place the nuclear transport signal at nucleotide +1158 with respect to the adenine nucleotide of the start codon of the LacI gene in the pI$^q$Py1A template. This construct has been designated pPy(SL)SS1A as shown in FIG. 1.

TABLE 1

Polynucleotides Used To Insert The Nucleic Acid Coding For The Nuclear Transport Signal Polynucleotide P1 - 5' Lac I Gene Location 5'- A ACG TTA CTG GTT TAA CCT TCC TCT TCT TCT
TAG GCA TGG TGG GAG GGT ACC TCT AGA -3'
(SEQ. ID No. 6)

Polynucleotide P2 - 3' Lac I Gene Location

ATT GCG TTG CGC AAC CTT TCA CCT CTT CTT CTT
AGG AGG CCT CAG GCT GCT CTG CCC GCT TTC
CAG -3'
(SEQ. ID No. 7)

The site-directed mutagenesis reaction used to place the nuclear transport signal at these positions was carried out in the following manner to produce individual construct having the nuclear transport signal-coding nucleic acid segment at different positions within the LacI gene. Briefly, 5 ug of the pI$^q$Py1A single-stranded template DNA prepared above was admixed with 50 ng of kinased polynucleotide P1 or P2 (Table I) that were synthesized on an Applied Biosystem oligonucleotide synthesizer (Foster City, Calif.), and were Kinased on the synthesized according to the manufacturers instructions, as a kinased polynucleotide to form a 10 ul admixture. This admixture was maintained at 68C. for 10 minutes and then 25C. for 5 minutes to allow the polynucleotide to anneal to the single-stranded template. The DNA strand containing either polynucleotide P1 or P2 (Table I) was synthesized by adding 4 ul of a solution containing 10 mM of adenosine triphosphate (rATP), 4 ul of a buffer containing 0.66M Tris HCl at pH 7.6, 50 mM $MgCl_2$, 50 mM dithiothreitol (DTT), 2 ul of a solution containing 2.5 mM each of dCTP, dATP, dGTP and dTTP, 1 ul of T4 DN4 ligase (Stratagene, La Jolla, Calif.), 1 ul of the Klenow fragment of DNA polymerase 1 (Stratagene, La Jolla, Calif.) to form a mutagenesis reaction admixture. This admixture was maintained at 25C. for three hours. The mutagenesis reaction was terminated by adding 1 ul of a solution containing 50 mM ethylene diamine tetraacetic acid (EDTA).

The mutagenesis reaction admixture (10 ul) was then transformed into competent XL1-blue host cells using the instructions provided by the manufacturer of these competent cells (Stratagene). DNA was isolated from the resulting transformants using the DNA isolation procedures of Sambrook et al., *Molecular Cloning: A Laboratory Manual, Second Edition,* Cold Spring Harbor Laboratory, Cold Spring Harbor, New York, N.Y. (1989). The accuracy of the above site-directed mutagenesis procedure was confirmed by restriction endonuclease digestion.

The LacI plus nucleus-targeting signal sequence constructions were evaluated in vectors having bacterial promoters prior to construction of the eukaryotic vectors. An IPTG spot assay was performed on the bacterial vector constructs to measure levels of repression and inducibility of the vectors expressing the Lac repressor. For the assay, constructions were first transformed into a LacI-/LacZ bacteria and 200 ul of log phase culture of these cells were plated as an overlay on LB-amp agar. Upon hardening, 2 ul of 250 ug/ul X-gal and 10 ul of various concentrations of IPTG (0, 10, 20, or 50 nmoles) were spotted onto designated areas of the plate. After an overnight maintenance at 37C., the plates were examined and the minimum concentration of IPTG required for induction of beta-galactosidase (Lac Z) activity was determined. Constructs that produced a pale blue colony after treatment with IPTG were scored as inducible repressor constructs with the level of responsiveness (inductiveness) to IPTG being determined by the lowest concentration of IPTG required to derepress expression of the Lac Z gene and form the typical pale blue bacterial colony in the presence of X-gal. Although not shown, five constructs had been prepared using bacterial promoters in which the nucleic-targeting sequence had been placed in either the 5' or 3' regions of the lac-repressor four of the five constructs expressed inducible repressor in the bacterial IPTG spot assay: namely, three of four 3' constructs and the one 5' construct. One each of the 5' and 3' constructs were selected and manipulated to form the eukaryotic vectors pPyS'SS1A and pPy(SL)SS1A.

The IPTG spot assay is therefor a useful screening step in the preparation of inducible repressor constructs having a nucleus-targeting amino acid residue signal sequence. The assay serves to identify constructs able to express a repressor polypeptide capable of repressing the lac operon and induction in the presence of specific inducers.

2. Preparation of rDNA Molecule Coding for a Lac Operator-Regulated Luciferase Protein A. Luciferase Expression Vector The luciferase expression vector, pRSVLuc, was constructed using standard molecular biology techniques and the entire DNA sequence of that vector is listed in SEQ. ID No. 5. The luciferase expression vector has at nucleotides number 2106–2627 the RSV promoter sequence, and exon from SV40 at nucleotides 2637–2670, an SV40 intron at nucleotides 2671–2759, the luciferase gene at nucleotides 2975–4822, the polyadenylation signal sequence at nucleotides 4823 to 5166, and the transcription start sequence begins at nucleotide 2595.

B. Lac Operator-Regulated Luciferase Expression Vectors

Figure 2:
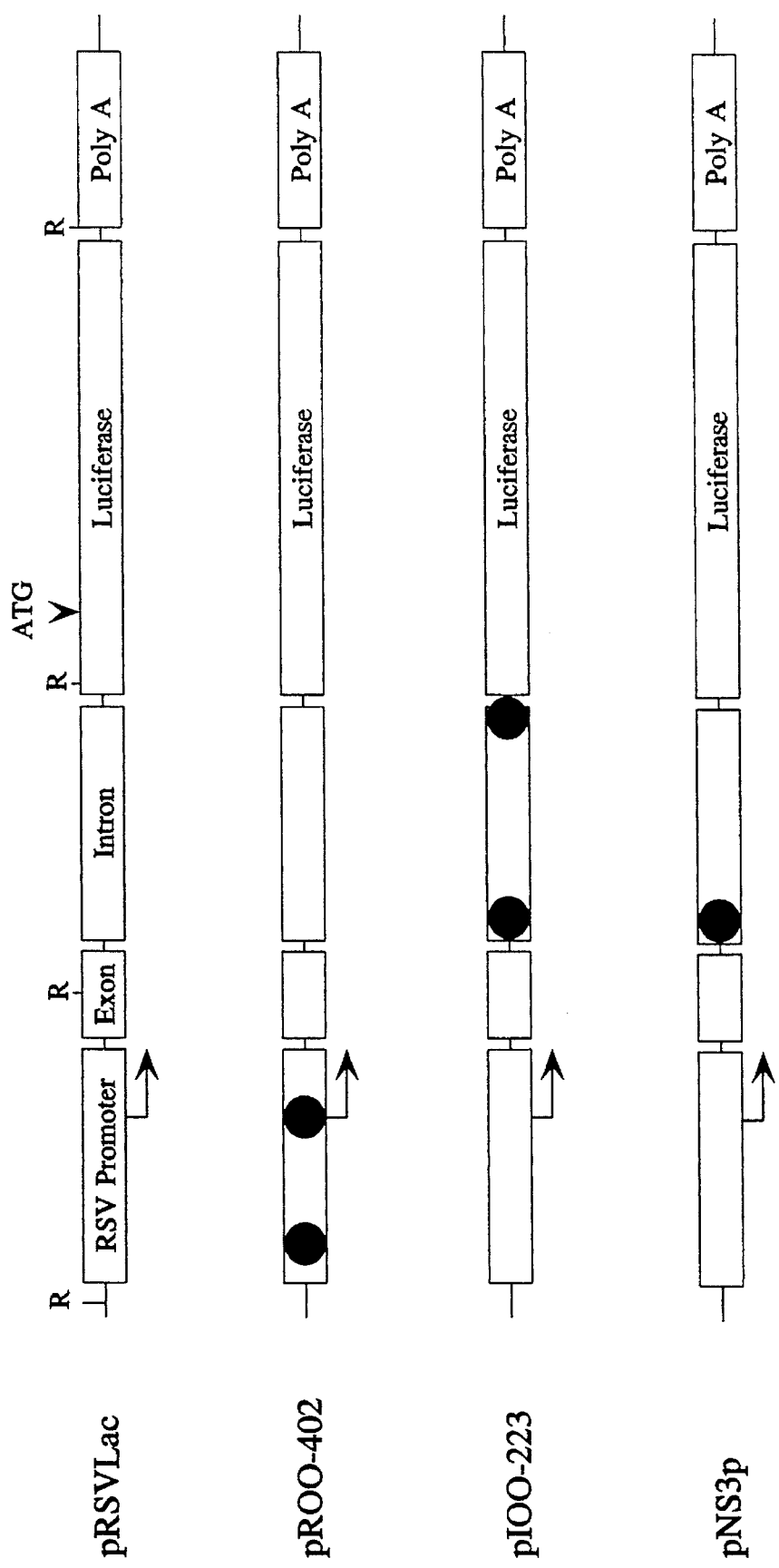
In FIG. 2, a schematic of the various features of the Lac operator-regulated luciferase expression vectors is shown. The RSV promoter, the SV40 intron, the luciferase gene and polyadenylation signal are shown. The ideal operator (closed circle), the 18-mer operator (dotted circle) and the wild type operator positions are also shown.

The luciferase expression vector described above was modified to insert the wild type Lac operator sequence or the tight binding Lac operator sequence described by Saldler et al., *Gene,* 8:279 (1980) into the either the RSV promoter or the intron between the promoter and the luciferase gene of the pRSVLuc plasmid at various locations. This construct is shown in FIG. 2. To facilitate the construction of these modified plasmids a Spe I endonuclease recognition sequence was introduced into the pRSVLuc plasmid using site-directed mutagenesis performed using the Mutator™ site-directed Mutagenesis Kit (Stratagene) and the manufacturer's instructions provided with that kit.

Briefly, the uracil-containing single-stranded template required for the site-directed mutagenesis procedure was prepared first by maintaining a 5 ml culture of XL1-blue cells (Stratagene) containing the pRSVLuc plasmid at 37C. for 3 hours. One ul of a solution containing $1\times10^{11}$ plaque forming units (pfu) per ml of VCS-M13 helper phage (Stratagene) was then added to the 5 ml culture and the culture was further maintained at 37C. for 3 hours. During this time, single-stranded M13 phage containing the single-stranded pRSVLuc DNA are formed and released from the XL1-blue bacteria.

The bacteria in this culture were killed by heating the culture to 68C. for 15 minutes. The killed bacteria were removed from culture, by centrifuging the culture at 10,000×g to produce a supernatant containing the pRSVLuc single-stranded phage. One ml of this supernatant was added to a previously established 5 ml culture of CJ236 bacteria (Biorad Laboratories, Richmond, Calif.) that was in the late log phase of growth. The culture was maintained at 37C. for 10 min. and then 10 ul of the culture was plated onto LB bacterial plates containing both 50 ug/ml of ampicillin and 30 ug/ml of chloramphenicol. The resulting bacterial plates were maintained at 37C. for 12–18 hours to allow individual colonies of CJ236 bacteria containing the pRSVLuc single-stranded M13 phage to form.

One of the resulting colonies was selected and used to initiate a 5 ml bacterial culture in superbroth media. This 5 ml culture was maintained at 37C. for 6 hours and then transferred to 250 mls of superbroth in a 250 ml flask and further maintained at 37C. for one hour with constant shaking. Then 100 ul of a solution containing $1\times10^{11}$ PFu/ml of VCS-M13 helper phage (Stratagene) was added to the culture and the culture was maintained at 37C. for 12–18 hours with constant shaking. During this time, a culture of CJ236 bacteria containing the PRSVLuc single-stranded DNA template was produced.

This culture was then used to isolate the PRSVLuc single-stranded template using the single-stranded phage DNA isolation procedures described in the pBluescript® II manual (Stratagene). Briefly, 50 μl of the culture containing PRSVLuc single-stranded phage produced above was centrifuged at 17,000×g to produce a clarified supernatant. Approximately 1.2 ml of this supernatant was transferred to an eppendorf centrifuge tube and 300 ul of a solution containing 3.5M NH₄ Acetate at PH 7.5 and 20% polyethylene glycol (PEG) was admixed to it. The resulting admixture was maintained at 25C. for 15 minutes. The admixture was centrifuged at 11,000×g for 20 minutes to pellet the single-stranded phage present. The resulting supernatant was removed from the phage pellet.

The phage pellet was resuspended in 300 μl of TE buffer consisting of 10 mm Tris-HCl at pH 8.0 and 1 mm EDTA. The resulting solution was admixed with an equal volume of phenol/chloroform and the resulting aqueous phase transferred to a fresh tube. The aqueous phase was reextracted with phenol/chloroform until no significant interface between the organic and aqueous phase was observed. The aqueous phase was then admixed with an equal volume of chloroform and the single-stranded DNA isolated from the aqueous phase by ethanol precipitation using Ammonium Acetate.

The amount of single-stranded PRSVLuc DNA isolated was determined by gel electrophoresis. This single-stranded pI$^q$Py1A DNA was then used as a template in the site-directed mutagenesis procedure below.

The Spe I restriction endonuclease recognition sequence was then inserted into the pRSVLuc DNA sequence at different locations in individual constructs using the pRSV-Luc single-stranded DNA template prepared above and the polynucleotides listed in Table II and the site-directed mutagenesis protocol described above.

Each of the four polynucleotides listed in Table II was used to produce a modified pRSVLuc plasmid having the Spe I restriction endonuclease recognition site located at a different position. Polynucleotide BP 2166 was used to place the Spe I restriction endonuclease site at nucleotide 2166 of the pRSVLuc plasmid. Polynucleotide BP 2674 was used to place the Spe I restriction endonuclease site at nucleotide 2674 of the pRSVLuc plasmid.

Polynucleotide BP 2899 was used to place the Spe I restriction endonuclease site at nucleotide 2899 of the pRSVLuc plasmid.

The site-directed mutagenesis reaction used to place the Spe I restriction endonuclease site at these positions was carried out in the following manner to produce individual constructs having the Spe I restriction endonuclease recognition sequence at different positions within the pRSVLuc plasmid. Briefly, 5 ug of the pRSVLuc single-stranded template DNA prepared above was admixed with 50 ng of one of kinased polynucleotides listed in Table II that was purchased as a kinased polynucleotide to form a 10 ul admixture. This admixture was maintained at 68C. for 10 minutes and then 25C. for 5 minutes to allow the polynucleotide to anneal to the single-stranded template. The DNA strand containing the polynucleotide of Table II was synthesized by adding 4 ul of a solution containing 10 mM of adenosine triphosphate (ATP), 4 ul of a buffer containing 0.66M Tris HCl at pH 7.6, 50 mM $MgCl_2$, 50 mM dithiothreitol (DTT), 2 ul of a solution containing 2.5 mM each of dCTP, dATP, dGTP and dTTP, 1 ul of T4 DNA ligase (Stratagene), 1 ul of the Klenow fragment of DNA polymerase 1 (Stratagene, La Jolla, Calif.) to form a mutagenesis reaction admixture. This admixture was maintained at 25C. for three hours. The mutagenesis reaction was terminated by adding 1 ul of a solution containing 50 mM EDTA.

The mutagenesis reaction admixture (10 ul) was then transformed into competent XL1-blue host cells using the instructions provided by the manufacturer of these competent cells (Stratagene). DNA was isolated from the resulting transformants using the DNA isolation procedures of Sambrook et al., *Molecular Cloning: A Laboratory Manual, Second Edition,* Cold Spring Harbor Laboratory, Cold Spring Harbor, New York, N.Y. (1989). The accuracy of the above site-directed mutagenesis procedure was confirmed by restriction endonuclease digestion.

TABLE II

| Oligos[a] for Insertion of Spe I Restriction Site |
|---|
| BP 2166: 5'-ACA AGG CAA GAC TAG TCC GAC AAT TG-3' |
| BP 2567: 5'-TTT AAG TGC CTA CTA GTA TAC AAT AAA C-3' |
| BP 2674: 5'-AAT ATA AAA TTT ACT AGT GTA TAA TGT GTT-3' |
| BP 2899: 5'-CTC CTG GTG GAC TAG TTC AAA GAA CT-3' |

[a]The nucleotide sequence for BP 2166, 2567, 2674 or 2899 are also contained in SEQ. ID NOS. 8, 9, 10 or 11, respectively.

Individual modified pRSVLuc constructs having a Spe I restriction endonuclease recognition sequence at nucleotide positions of 2910 and 2579 were digested with Spe I (Stratagene) restriction endonuclease using condition recommended by the enzyme's manufacturer. The two polynucleotides, IO1 and IO2 were annealed together by admixing 50 ng of each polynucleotide in a solution containing 50 mM Tris-Hcl at pH 7.4 7 mM MgC2l and 1 mM dithiothreitol. This solution was then maintained at 68C. for 10 minutes and then 25C. for 15 min. The resulting double-stranded polynucleotide was ligated (operatively linked) into the Spe I-cleaved modified pRSVLuc plasmid. The accuracy of these construction steps was confirmed by DNA sequencing.

A second ideal operator was added to each of the above constructs to produce modified pRSVLuc plasmids having two operator sequences at nucleotide positions 2687 and 2910 in pI00-223 and at nucleotide position 2177 and 2579 in pR00-402 as shown in FIG. 2. These second operator sequences were added by preparing single-stranded template from each of the single operator-containing constructs prepared above. An additional Spe I restriction endonuclease site was added using the appropriate polynucleotide of Table II and the site-directed mutagenesis procedure described above. After the second Spe I site was confirmed by restriction digests, the second operator-containing was ligated into the plasmid.

The modified pRSVLuc plasmid, pNS3P has an 18-mer operator sequence located at nucleotide position 2687 as shown in FIG. 2. The pNS3P plasmid was produced by introducing a Spe I restriction endonuclease recognition sequence at the appropriate position using polynucleotide BP 2674 of Table I and the site-directed mutagenesis procedure described above. The resulting modified pRSVLuc construct was cleaved with Spe I and then purified for use in a ligation reaction. The double-stranded 18-mer operator insert is formed by annealing polynucleotides 18(1) and 18(2) of Table III and ligating it into the Spe I cleaved modified pRSVLuc plasmid. The resulting construct has the 18-mer operator located at nucleotide position 2687 and is pNS3P.

TABLE III

Polynucleotides used to insert various operator sequences

Polynucleotide IO1 - Ideal Operator (−) strand
5'-CTA GGG TCG ACT GTG GAA TTG TGA GCG CTC
ACA ATT CCA CAA C-3' (SEQ. ID NO. 12)
Polynucleotide IO2 - Ideal Operator (+) strand
5'-CTA GGT TGT GGA ATT GTG AGC GCT CAC AAT
TCC ACA GTC GAC C-3' (SEQ. ID NO. 13)
Polynucleotide 18(1) - 18-mer Palindromic Operator (−) strand
5'-CTA GGG TCG ACA TTG TGA GCG CTC ACA ATC-3'
(SEQ. ID NO. 14)
Polynucleotide 18(2) - 18-mer Palindromic Operator (+) strand
5'-CTA GGA TTG TGA GCG CTC ACA ATG TCG ACC-3'
(SEQ. ID NO. 15)

3. In Vitro Regulated Expression of Luciferase in Eukaryotic Cells

A. Transfection to Form Stably Integrated Lac Repressor Expression Vectors

NIH3T3 cells were stably transfected using Stratagene's Mammalian Transfection Kit (Stratagene, INC., La Jolla, Calif.). For the transfection, $5 \times 10^5$ NIH3T3 cells were plated in 100 mm culture dishes and maintained overnight at 37C. Both pPy5'SS1A and pPy(SL)SS1A expressing lac repressor and nuclear transport signal-coding nucleic acid segment prepared in Example 1b were used for transfection. Twenty micrograms of plasmid DNA prepared according to standard procedures was admixed with 50 ul of 2.5M $CaCl_2$ and 500 ul of 2×N,N-bis (2-hydroxyethyl)-2-aminoethanesulfonic acid/saline and maintained for 20 minutes at room temperature. The admixture was then applied dropwise to separate aliquots of attached NIH3T3 cells to form a cell-DNA admixture which was maintained overnight at 37C. and 4% $CO_2$ to form transfected NIH3T3 cells.

The cell admixture was then washed twice with phosphate buffered saline (PBS), resuspended in fresh DMEM media and then added back to the culture plates. The cells were maintained overnight at 37C. and 7% $CO_2$ after which time the cells were split 1:10 and maintained another 24 hours before 400 ug/ml hygromycin was admixed to the adhered cell for selection of stable mutants (Hyg R). Approximately six stable clones from a possible 50 to 100 hygromycin resistant clones on each plate were isolated about 14 days after transfection. Each of the selected clones were expanded to $1 \times 10^6$ cells and examined for expression of a functional repressor as performed below.

For detecting LacI in transfected cells, a gel shift assay was used. Functional lac repressor in both isolated cytosolic and nuclear cell fractions was measured by mixing the extracts from $1 \times 10^6$ stably transfected NIH3T3 cells as prepared above with 3 ng of $^{32}$P-labeled lac operator oligonucleotide. Thirty percent of the total extract was loaded per well. Binding was detected by a shift in the gel position of the double stranded oligonucleotide during electrophoresis on native acrylamide gels.

Five ng of purified wild type lac repressor was readily detected by this assay. The migration of bands from nuclear signal-transport sequence transfected cell extracts was slower than that of the wild type, consistent with the effects of the addition of the positively charged signal sequence. Untransfected cells did not contain a gel shifted fragment in the nuclear fraction. The ratios of the amount of lac repressor in the nucleus versus the cytosolic fraction was approximated by visual determination. No increase in the intensity for any of the cytosolic bands in transfected or untransfected cells was seen. The gel shift assay provides a means to measure the effectiveness in transfected aukaryotic cells of the position of the operatively linked nuclear signal-transport sequence within a nucleus-targeted inducible repressor polypeptide of this invention.

B. Transient Transfection of Luciferase Expression Vectors—Lac R(S) & Lac O(T)

Stably transfected clones expressing lac repressor prepared above were then transiently transfected with plasmids prepared in Example 2b containing lac operator sequences and expressing luciferase. The plasmids transfected were pRSVLuc, pR00-402, pNS3P and pI00-223. The transfections were performed as described for stable transfections with the exception that after washing the NIH3T3 cells transfected with 20 ug of lac operator-regulated luciferase expressing plasmid, the plates were maintained until a confluent culture was obtained approximately 48 to 72 hours later. Duplicate plates were prepared for each luciferase plasmid transfected into the NIH3T3 cells. One plate of each duplicate set contained 40 mM IPTG as an inducer.

After the cells reached confluency approximately at $5 \times 10^6$ cells, they were harvested in 1 ml PBS using a rubber policeman. For each plate of cells, one half of the total number of cells after harvesting was used for the preparation of cell extracts for luciferase assays described in Example 3e.

The remaining harvested cell preparation for each selected clone was used to determine copy number of the transiently transfected plasmid. The Hirt procedure for DNA extraction was followed. The harvested cell suspension was admixed with 1 ml of 0.6% sodium dodecyl sulphate, pH 7.5, containing 0.01 M EDTA and the admixture was maintained at 20 minutes at room temperature to form a cell lysate. To the cell lysate, 5M NaCl was admixed to a final concentration of 1M and inverted 10 times. After maintaining the admixture overnight at 4C., it was centrifuged at 10,000 rpm to form a cell lysate pellet. The resultant supernatant containing DNA was collected and an aliquot was then applied to a nitrocellulose slot blot for immobilization of the DNA following standard protocols. A $^{32}$P labeled luciferase fragment was then hybridized to the prepared nitrocellulose slot blots. Copy number of the luciferase gene was determine by comparing the intensity of the hybridized area to control samples. The estimated number of transfected plasmid per cell was greater than 100 copies. The results of the luciferase assays determining the level of expression is shown below in Example 3D in Table IV.

Using the above methods of transient transfection of a reporter gene expression vector, one can screen vectors produced having an operator in any of a variety of locations as described herein, to determine optimum placement of one or more operators within the operator-regulated gene expression DNA segment of this invention.

C. Stable Transfection of Luciferase Expression Vectors—Lac R(S) & Lac O(S)

Stably transfected clones expressing lac repressor prepared above are stably transfected with plasmids containing lac operator sequences and expressing luciferase prepared in Example 2b. The transfection and isolation procedure is performed as described above for stable transfection of NIH3T3 cells with plasmid DNA expressing lac repressor. Approximately six stable clones from each plate of individual transfections are expanded to 1×10⁶ cells and treated with IPTG to test for induction as performed below.

D. Luciferase Assay to Detect Induction

The harvested cell pellets (1×10⁶ cells) prepared above were resuspended in 100 ul 100 mM KHPO$_4$, pH 7.8, 1 mM DTT and freeze/thawed 3 times using dry/ice ethanol and 37C. water baths. The resuspended cell pellets were then centrifuged at 10,000 rpm for 5 minutes and the supernatant was collected. Protein content and luciferase production were determined, respectively, in the supernatant using the Stratagene Protein Assay Kit (Stratagene) and the luciferase luminometer assay described below.

The ILA911 luminometer (Tropix, Bedford, Mass.) was primed with a 1 mM D-Luciferin/dH$_2$O) solution (Analytical Luminescence, San Diego, Calif.). 150 ul of 100 mM KHPO$_4$, pH 7.8, 3.65 mM ATP, 21 mM MgCl$_2$ was placed in 12×75 mm polystyrene sample cuvettes to which 10 ul of the cell extract supernatant prepared above was admixed. The cuvettes were placed into the luminometer, 100 ul of the above luciferin solution was injected to start the reaction, and emitted photon were recorded over 10 seconds. Luciferase production in the various transfections was compared after normalizing for protein content and copy number.

The results of the luciferase assays for transient transfections of the luciferase expression vectors, pR00-402, pNS3P and pI00-233 into either pPy5'SS1A or pPy(SL)SS1A stably transfected NIH3T3 cells are shown below in Table IV. Luciferase production by the various luciferase expression vectors with and without induction with IPTG was compared to transfections without any DNA or with wild type pRSVLuc. Induction was greatest with the pI00-233 luciferase expression vector where the ideal Lac operator sequence was located at the 5' and 3' end of the intron. This was the case with either repressor vector although with pPy5'SS1A where the nuclear signal-transport sequence was at the 5' end was 3-fold more efficient. A smaller induction was seen when the ideal operator sequence was within the RSV promotor region (pR00-402) and when the 18-mer palindromic operator sequence was located at the 5' end of the intron. IPTG treatment of cells transfected with the wild type pRSVLuc vector lacking an operator with either stably transfected repressor vector resulted in negative induction.

TABLE IV

| Repressor vector stably transfected: pPY5'SS1A | | | |
|---|---|---|---|
| Operator Vector | *RLU'S | RLU'S + IPTG | Fold Increase |
| No DNA | 193 | 216 | — |
| pRSVLuc | 3341947 | 2289118 | (−1.4) |
| PROO-402 | 9516 | 72733 | 7.6 |
| pNS3P | 35540 | 165762 | 4.7 |
| pIOO-223 | 2732 | 165430 | 60.0 |
| Repressor vector stably transfected: pPy(SL)SS1A | | | |
| Operator Vector | RLU'S | RLU'S + IPTG | Fold Increase |
| No DNA | 182 | 175 | — |
| pRSVLuc | 149214 | 91811 | (−1.6) |
| pROO-402 | 10689 | 40640 | 3.8 |
| pNS3P | 2194 | 67052 | 3.0 |
| pIOO-223 | 1379 | 23324 | 17.0 |

*RLU = relative light unit

4. Preparation of a Transgenic Mouse

A. Transgenic Mouse Having an Inducible Repressor-Coding Transgene

For the creation of a transgenic mouse having an inducible repressor-coding transgene, single cell mouse embryos were harvested from female mice, C57B16/J strain (Taconic Labs, Germantown, N.Y.), that were impregnated the evening before harvest. The harvested embryos were then treated with a solution of hyaluronidase and briefly cultured in M16 medium. The embryos were subsequently transferred to M2 medium retained on a microscope glass depression slide and were observed with a 40× objective and a 10× eyepiece through a Nikon Diaphot microscope equipped with Hoffmann optics. For injection of a solution of DNA as prepared below, the embryos were held in place with a holding pipet rounded with a microforge. Micromanipulators controlled the holding pipet and the injection pipet.

The pI$^q$Py1A vector, prepared as described in Example 1a, was digested with the restriction enzymes Bam H1 nd Csp45I to isolate the eukaryotic expression cassette, designed to express lac repressor driven by a F9-1 promoter. The 2.5 Kb fragment contains the Pyf9-1 promotor region, the LacI$^q$ gene, and the SV40 small intron and poly A addition signal from pMC1-neo. The fragment was separated on a 1% agarose gel and purified on glass beads using the Geneclean Kit® (BIO 101, Inc., La Jolla, Calif.). Briefly, the excised gel bank was admixed to 2.5 to 3 volumes of 6M NaI stock solution and maintained at 45C. to 55C. for 5 minutes to dissolve the agarose. A 1.25 ml Glassmilk suspension (specially prepared suspension or silica matrix) was admixed to the dissolved agarose DNA solution and maintained for 5 minutes at 25 to form a Glassmilk/DNA complex. The complex was centrifuged for 5 seconds to form a Glassmilk/DNA pellet which was washed 3 times with NEW (a concentrated solution of NaCl, Tris and EDTA). After washing, the DNA fragment was eluted from the Glassmilk into water or low-salt buffer.

The isolated DNA 2.5 kb Fragment, contained the F9-1 promoter, a polylinker region, the LacI gene with an ATG consensus translation start sequence, and an intron region followed by an SV40 polyadenylation signal. The DNA fragment was resuspended in water following purification to form a solution at a concentration of 5 ug/ml. Approximately 3 to 4 picoliters of the DNA fragment solution was injected into the male pronucleus of each embryo resulting in approximately 100 copies of DNA fragment into each embryo. A successful injection was monitored by visualizing a refractile change in the pronucleus. Four hundred to 500 harvested embryos were injected with the DNA fragment solution.

After injection, the embryos were transferred to M16 medium and maintained at 37C. in a 5% CO$_2$ atmosphere for 1 to 2 hours. Lysed embryos were removed from the medium and normal appearing embryos were transferred to the fallopian tube of pseudopregnant foster mothers. Approximately 200 viable embryos were obtained and 25 viable embryos were implanted into each of eight foster mouse mothers. The transfer of embryos into foster mothers anesthetized with avertin was performed under a dissecting microscope.

After birth, newborn mice were kept with the foster mother for 3 weeks at which point they were weaned and screened for DNA integration. Seven mouse pups were analyzed for the presence of the transgene. A 2 cm portion of the tail was removed and homogenized for a short duration in 2 ml of a solution of 0.1M NaCl, 50 mM Tris-HCl, pH 7.5, 1 mM EDTA. The resultant homogenized tissue was then treated with 50 ug/ml RNaseA and 0.1% SDS for 15 minutes at 37C. to form denatured RNA-free homogenate. The partially purified homogenate was then digested with Proteinase K for 3 hours at 55C. to form a genomic DNA-containing solution free of RNA and proteins. The genomic DNA solution was further purified with 3 phenol/chloroform extractions followed by ethanol precipitation. The purified genomic DNA was resuspended in water, digested with Bam HI restriction enzyme, and electrophoresed on a 0.8% agarose gel. The electrophoresed DNA was then denatured by soaking the gel in 1.5M NaCl, 0.5M NaOH for 1 hour and neutralized by soaking in 1.5M NaCl, 0.% M Tris-HCl, pH 7.4, for 30 minutes at room temperature. The treated gel was then washed in 10× SSC (1×=0.15M NaCl, 0.015M Na Citrate) and set up for Southern transfer as described in Maniatis, T. et al., *Molecular Cloning A Laboratory Manual*, pp. 109–110, 383–389, Cold Spring Harbor, N.Y. (1982).

The transfer filter, on which the digested genomic DNA was immobilized, was hybridized to randomly primed 32P-labeled DNA according to standard procedures. Maniatis, supra. Following overnight hybridization, the filter was washed in 0.1×SSC, 0.1% SDS and placed on Kodak XAR film in order to identify DNA present within the mouse genome. Standards of DNA used for microinjection were compared in intensity to the transgenic mouse bands to estimate copy number. From the seven mouse pups screened for the presence of the transgene, two animals were determined to contain the DNA.

Newborn mice determined to contain the transgene are mated and their progeny (F1) are examined for presence of the transgene. Approximately 50% of the F1 offspring typically express the transgene, demonstrating that the original transgenic mice carry the transgene in their germ line and that it is inherited normally.

5. In Vivo Uptake of Inducer is Tissue Specific

To demonstrate tissue specificity in whole animals of various inducers of the LacI gene, labeled dextran, IPTG, MTG, and glucose were separately injected intravenously into a mouse through the tail vein or intraperitoneally. The labelled inducers were injected intravenously into mice at the following concentrations: 3.5 uCi $^{14}$C-dextran (4.23 uCi/ml); 4.5 uCi $^{14}$C-IPTG (43 mCi/mmol); 2.5 uCi $^{14}$C-MTG (30 mCi/mmol); and 2.5 uCi $^{14}$C-glucose (50 mCi/mmol). Tissue and blood samples were isolated, weighed, and homogenized 1 hour and 4 hours following injection. Radioactivity levels were determined for each tissue and normalized to blood levels.

To confirm that the measured inducer uptake in whole animals was an indication of intracellular incorporation and not just a result of extracellular pooling, nuclear incorporation of inducer was examined. Nuclear and cytosolic concentrations of labeled inducer in liver and spleen cells were measured, with approximately 10% of the total counts for each tissue found in the nuclear fraction as seen below in Table V. This correlates with results of similar experiments in cultured cells. Absolute confirmation of MTG uptake was measured by subcellular fractionation of MTG-labeled cells. About 17% of total cellular material was found in the nucleus. Since the compound was shown to enter the cells, total counts were measured in the other tissues to estimate incorporation.

TABLE V

14C-MTG NUCLEAR ACCUMULATION IN COUNTS PER MINUTE

|  | CYTOSOLIC | NUCLEAR |
|---|---|---|
| LIVER | 32970 cpm | 2488 cpm |
|  | 19701 | 891 |
| SPLEEN | 3372 | 832 |
|  | 2558 | 133 |

Figures 1, 3A:
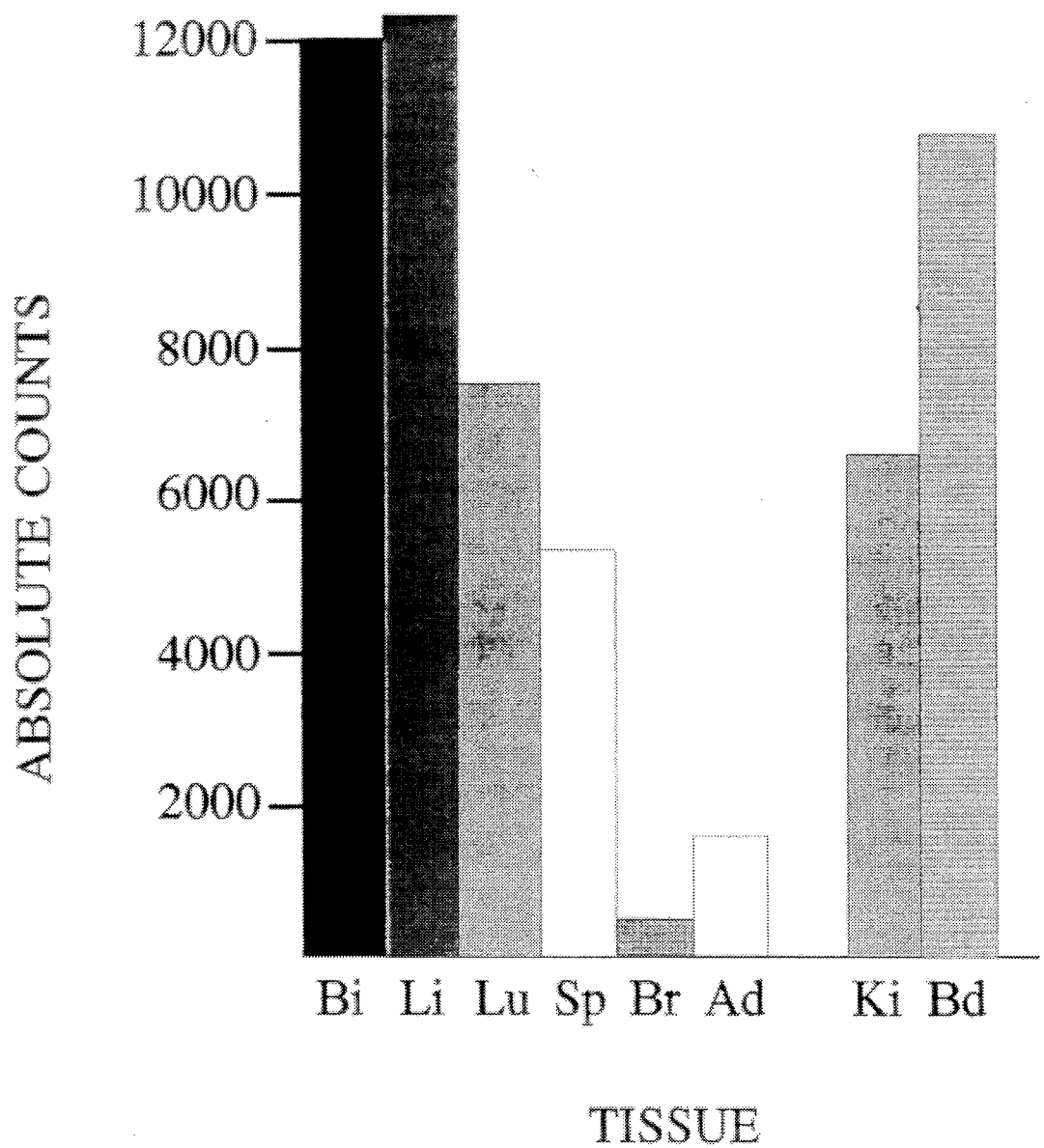
In FIGS. 3A (1–3), 3B (1–3), 3C (1–3) and 3D (1 and 2), the levels of radioactive inducer present in each tissue of a mouse injected with 3.5 uCi of $^{14}$C-dextran, 2.5 uCi of $^{14}$C-MTG; 4.5 uCi of $^{14}$C-IPTG and 2.5 uCi of $^{14}$C-glucose, respectively, are shown. The results, measured in absolute counts adjusted for volume, weight, and quenching, at 1 and 4 hours after intravenous injections are shown in panels A-1 and A-2, respectively. The results at 1 hour after intraperitoneal injections are shown in panel A-3. The results for intraperitoneal injections of labeled glucose are not shown. The tissues evaluated for radioactive inducer uptake included the following: bladder (Bl); liver (Li); lung (Lu); spleen (Sp); brain (Br); adipose (Ad); kidney (Ki); and blood (Bd). Standard deviation bars are shown for experiments repeated 3 or more times.
Figures 2, 3A:
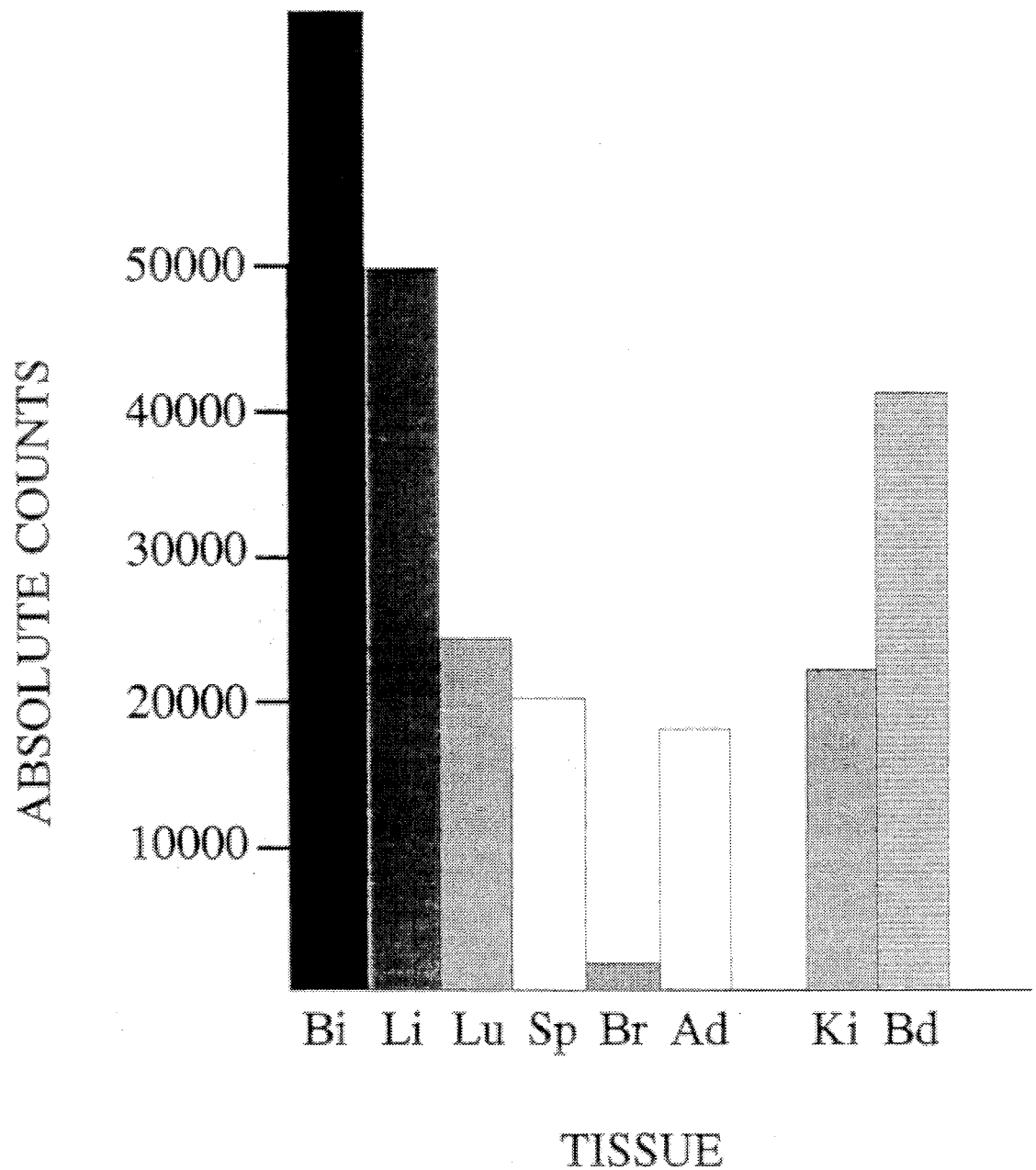
Figures 3, 3A:
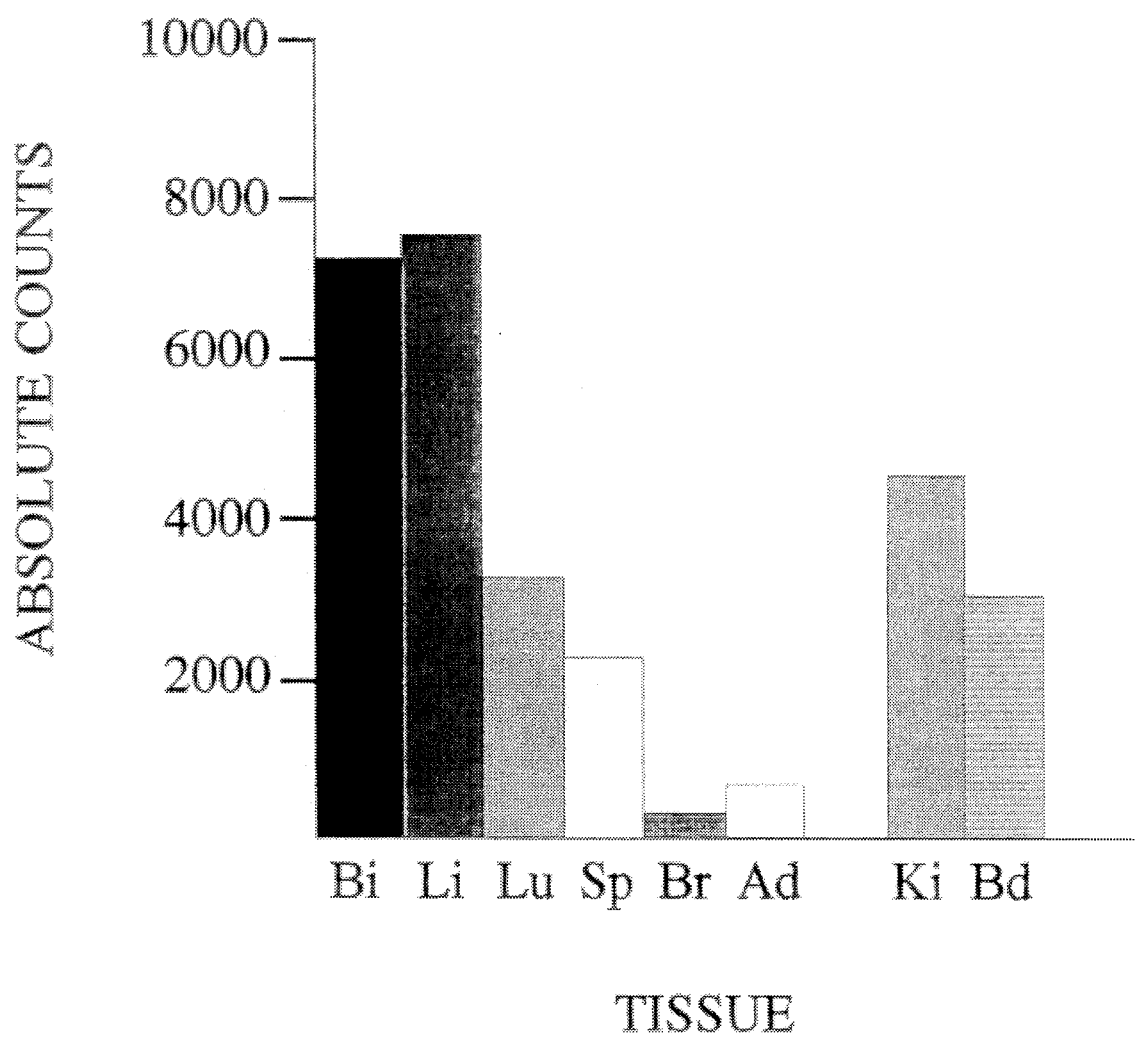

The results of these in vivo experiments on inducer specificity are shown in FIG. 3A. Based on results of similar experiments using an in vitro model with cell lines, inducer concentrations in tissue were expected to equilibrate to that in the blood. As the inducer was cleared from the blood through the kidneys, the levels within the tissues decreased at a given rate. Since the diffusion rate of the inducer from the tissues was likely to lag behind the blood clearance rate for extracellular inducer, inducer levels greater than that for inducer in blood was indicative of inducer tissue uptake.

Figures 1, 3B:
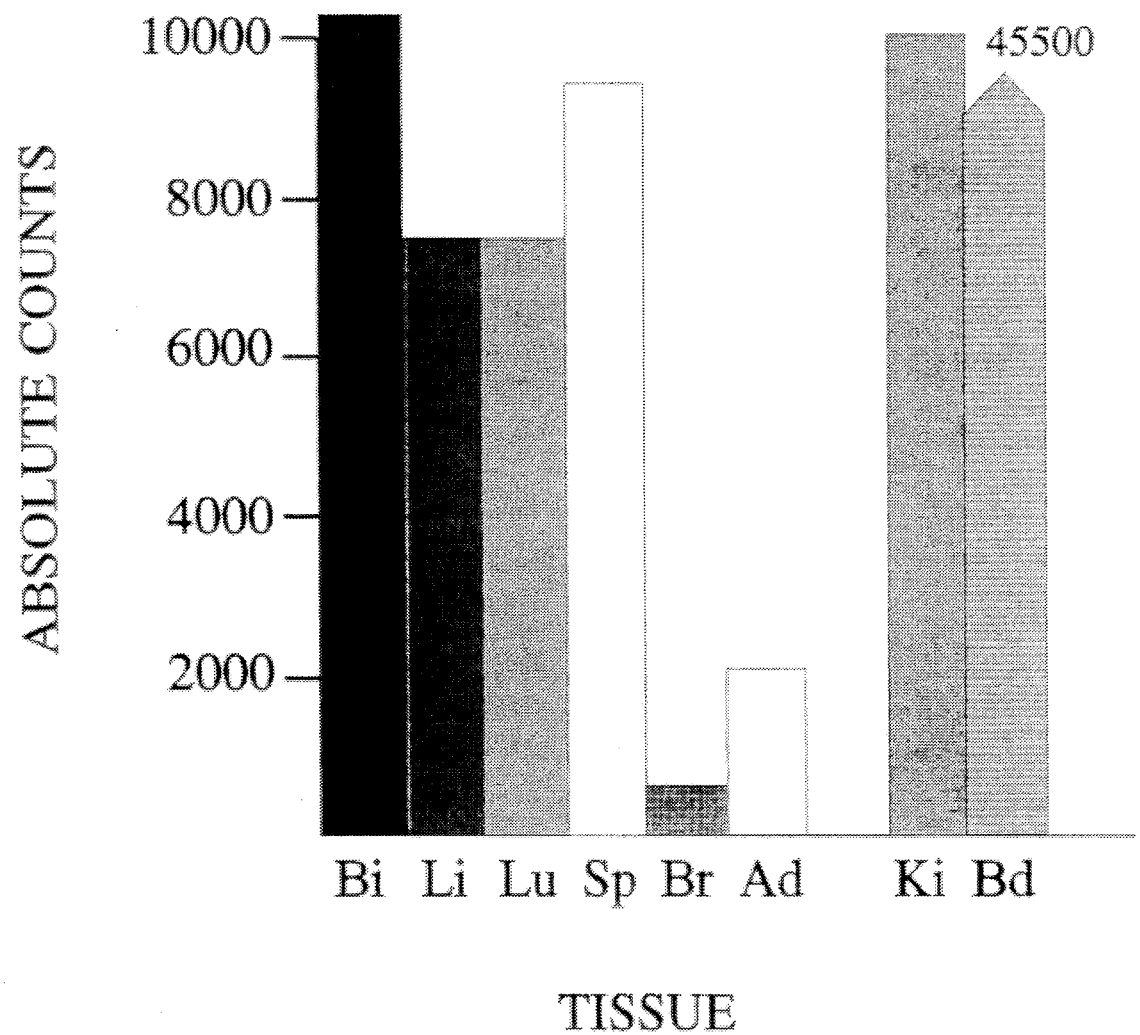
Figures 2, 3B:
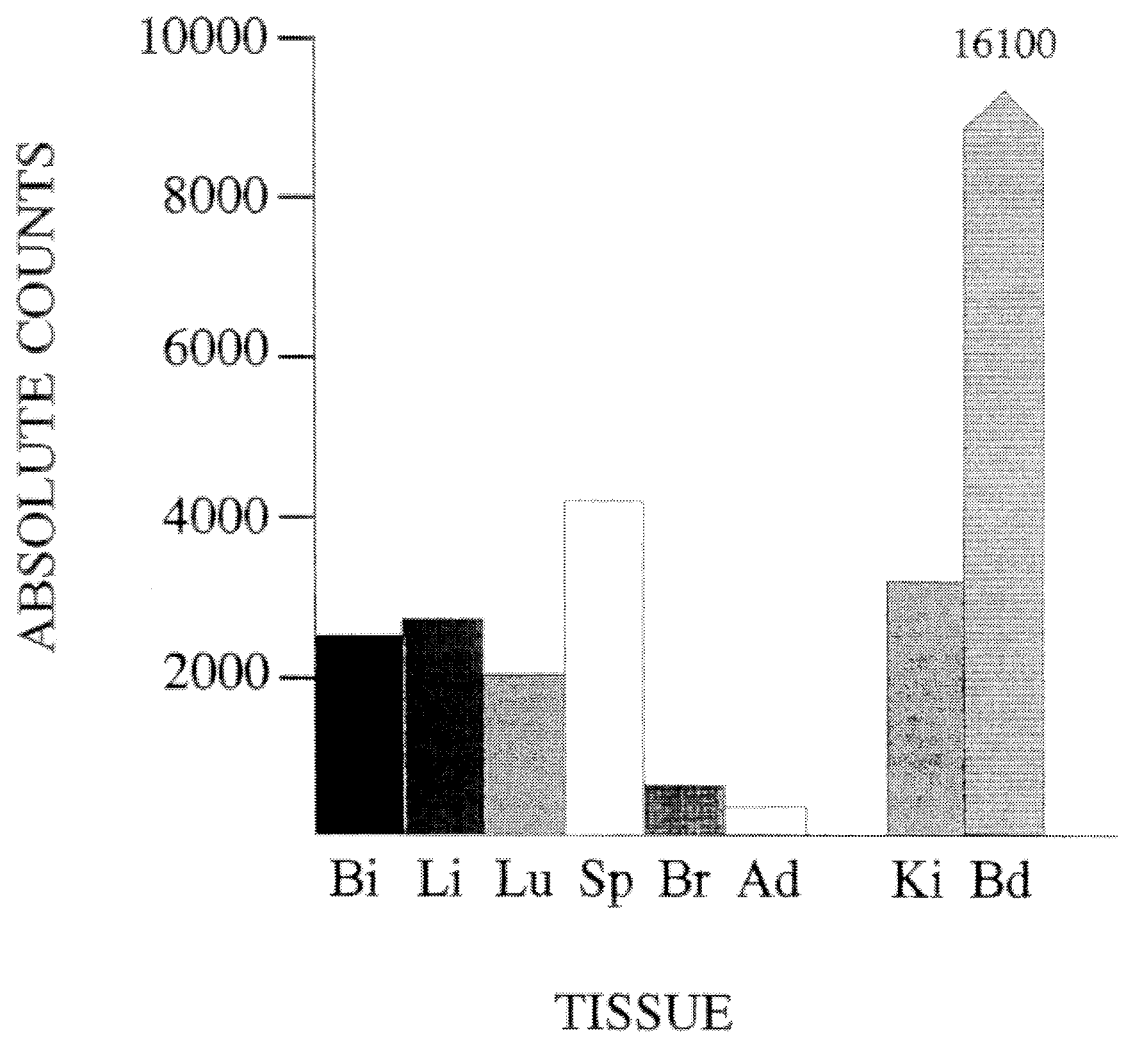
Figures 3, 3B:
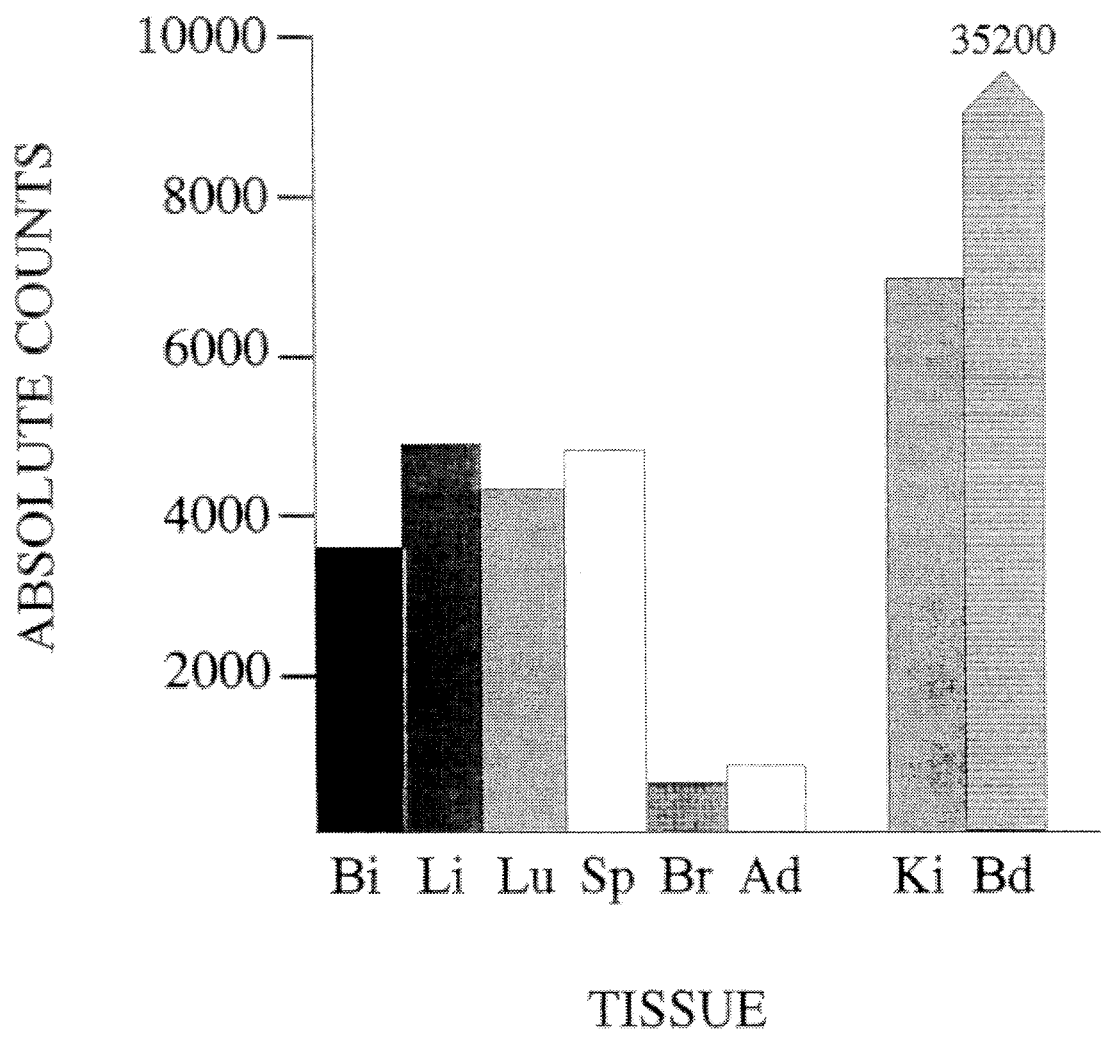
Figures 1, 3C:
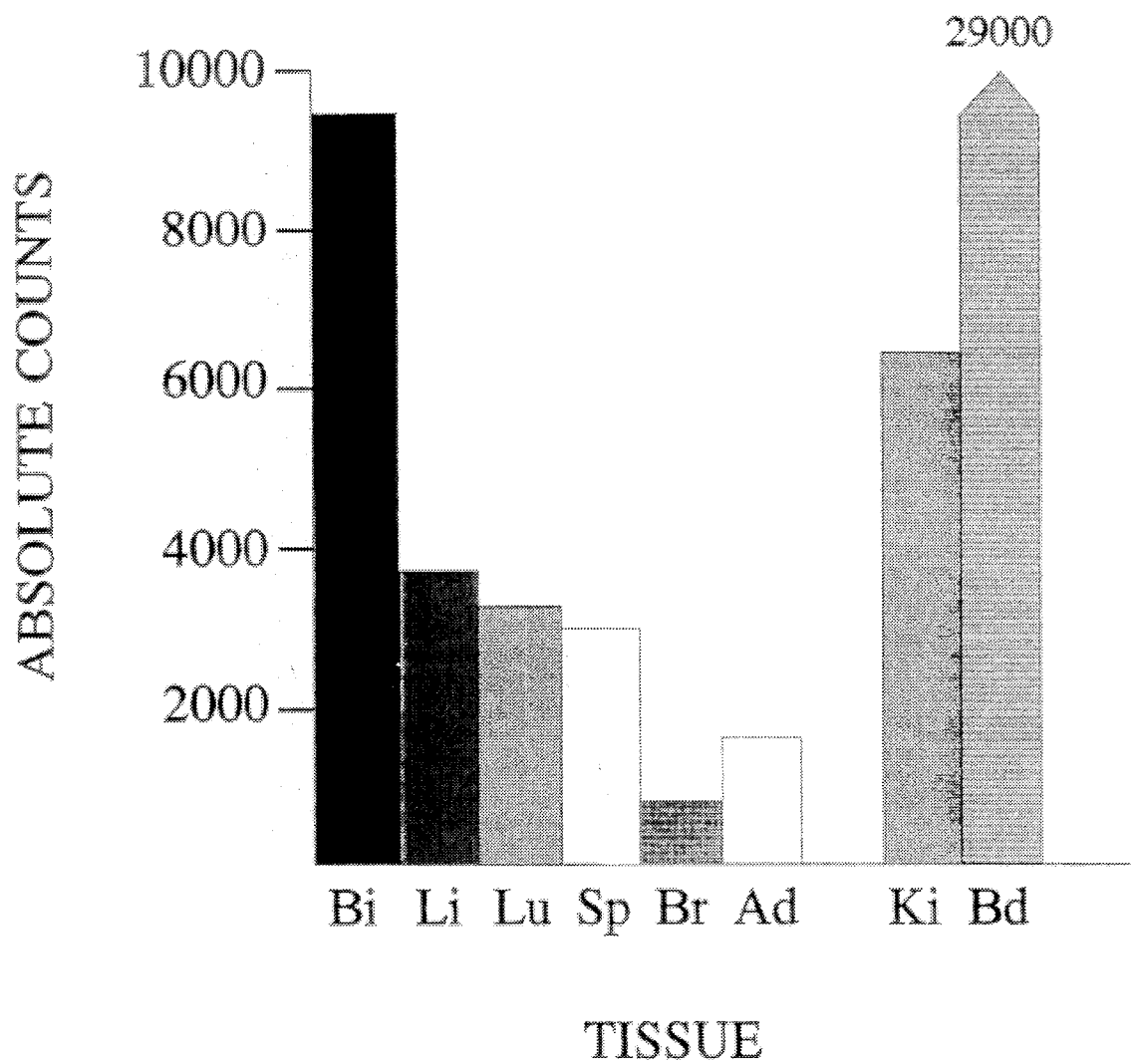
Figures 2, 3C:
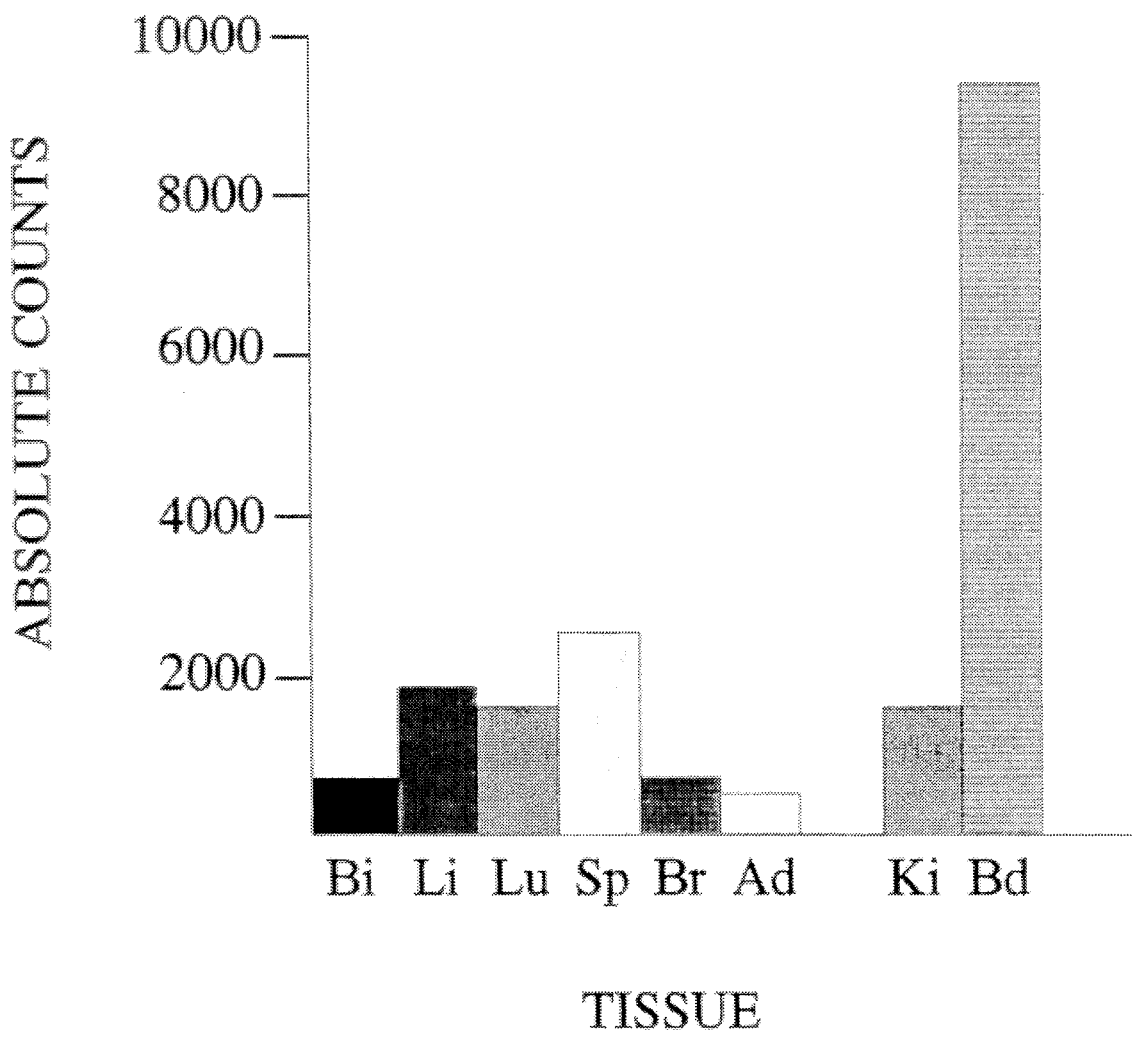
Figures 3, 3C:
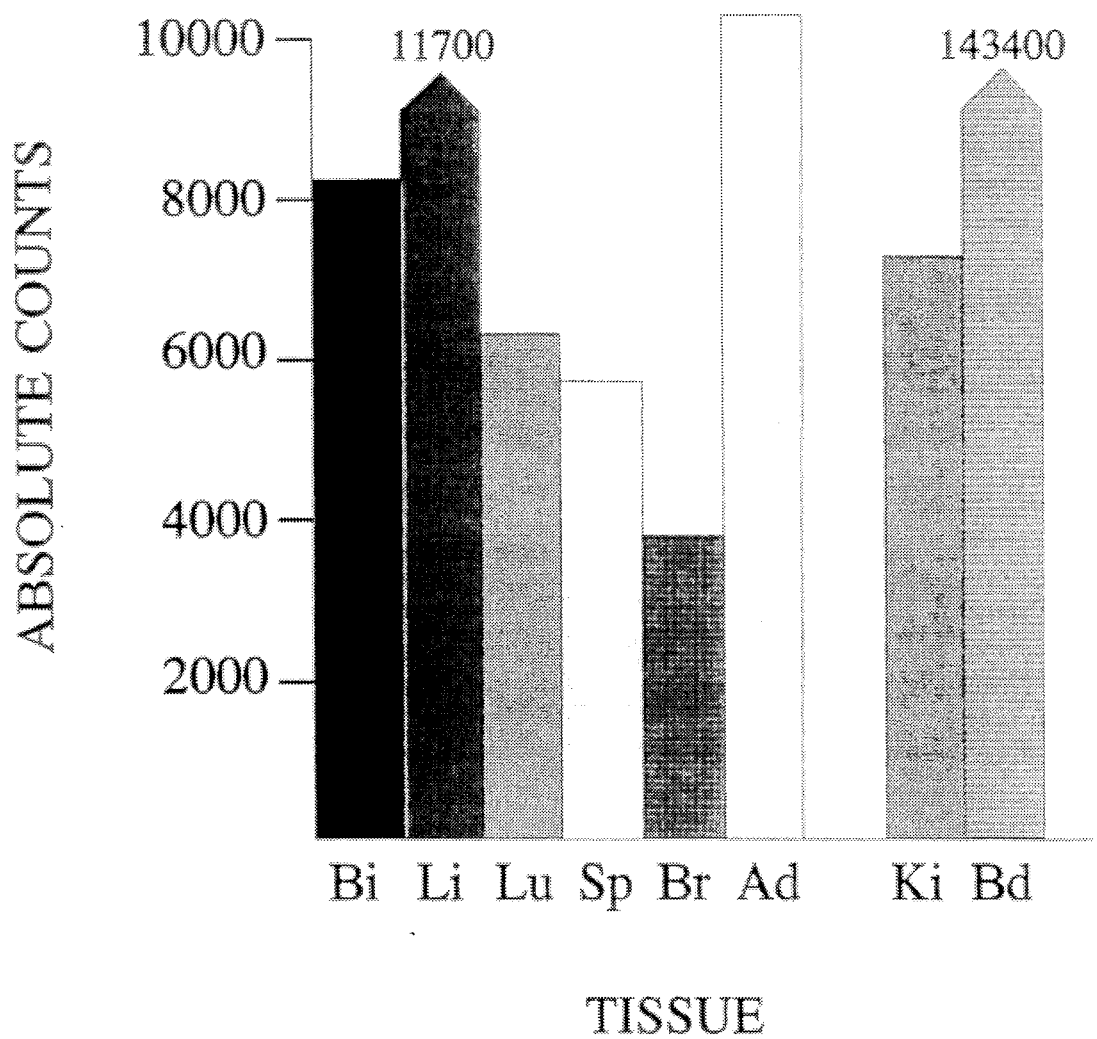

The results shown in FIG. 3A, B and C show the absolute levels of inducer uptake for various tissues, adjusted for volume, weight and quenching, as a function of blood levels at 1 and 4 hours following injection. Dextran was used as a measure of tissue vascular space and non-specific absorption since its size prevented it from being transported into the tissues. As shown in FIG. 3A, dextran uptake levels in all tissues were below blood levels. After 1 hour, high levels of MTG and IPTG were found in the kidney and the bladder, relative to other tissues, as a result of clearance of the compound from the blood via the kidneys. MTG and IPTG results are shown, respectively, in FIG. 3B and 3C. After 4 hours, IPTG accumulation in all tissues, except the brain and adipose, exceeded blood levels. Four hours following intraperitoneal injection of IPTG, inducer uptake levels in the liver, adipose and bladder were markedly higher than in the blood.

After 4 hours, MTG accumulated at higher levels in the liver and spleen than in the blood. Lower levels of MTG were seen in the adipose and brain, relative to other tissues. Intraperitoneal injection of MTG revealed accumulation in the liver, lung and spleen.

Figures 1, 3D:
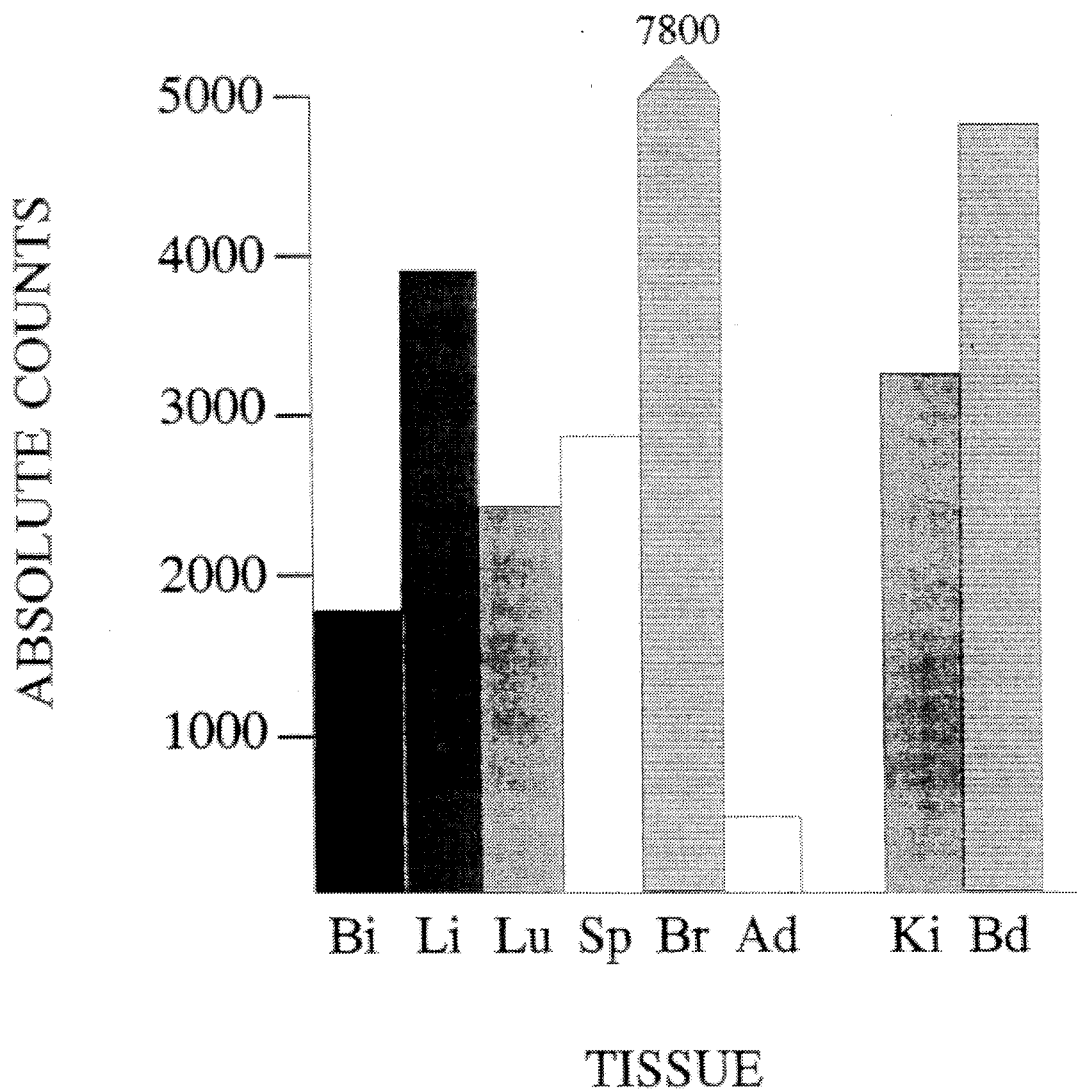
Figures 2, 3D:
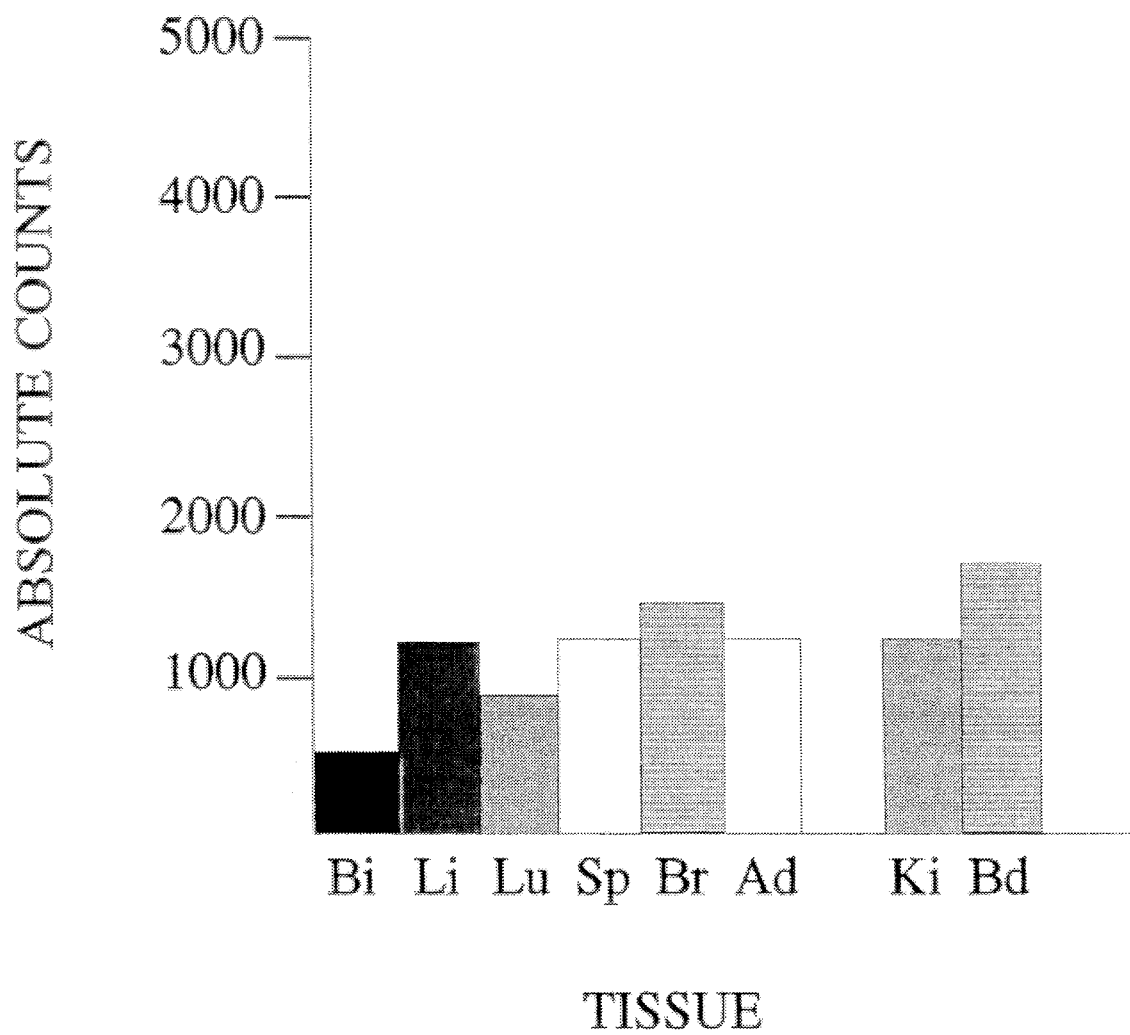

As a positive control for the experiments, the accumulation of labeled glucose was measured as it is actively transported into cells. Labeled glucose was detected at levels above the blood after both the 1 and 4 hour time points as shown in FIG. 3D. Glucose levels were significantly higher in the brain compared to the beta-galactosides which is consistent with the brain's selective use of glucose.

Figure 4A:
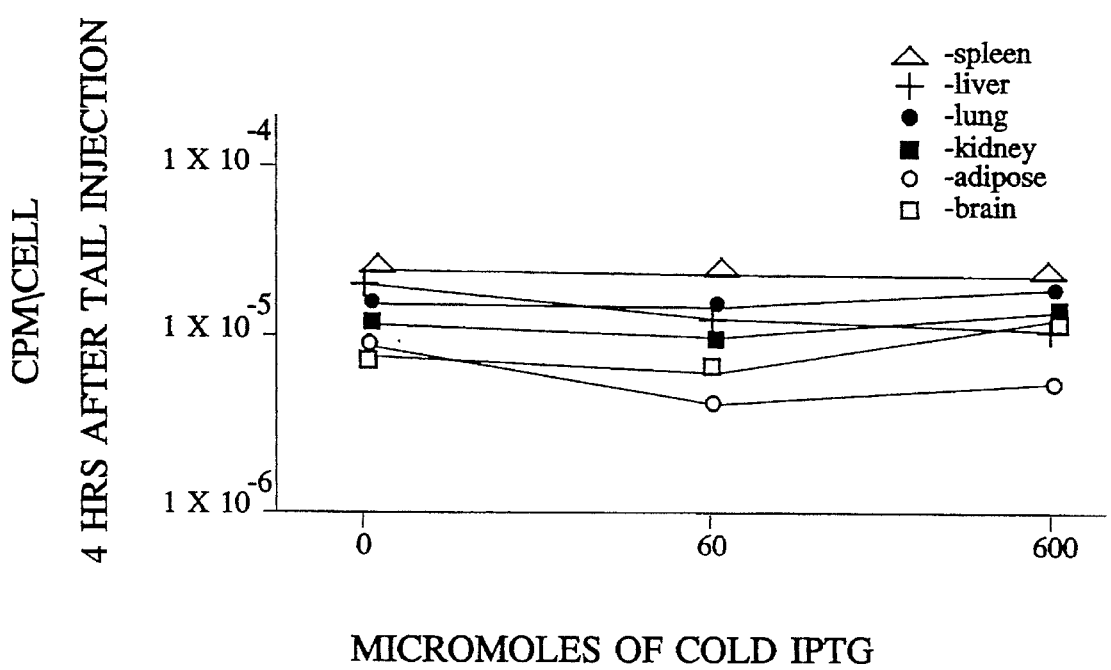
In FIG. 4 (A–B), the maximum levels of radioactive inducer which can be incorporated in each tissue of a mouse is shown. The results of injections with $^{14}$C-IPTG or $^{14}$C-MTG in the presence of increasing concentrations in micromoles (mM) of unlabeled inducer are shown in panels 4A and 4B, respectively. The radioactive inducer was intravenously injected as described in FIG. 3 and the saturation was measured 4 hours after injection. Counts per minute (cpm) per cell are graphed on the Y-axis against increasing concentrations from 0 to 600 mM of unlabeled inducer graphed on the X-axis.
Figure 4B:
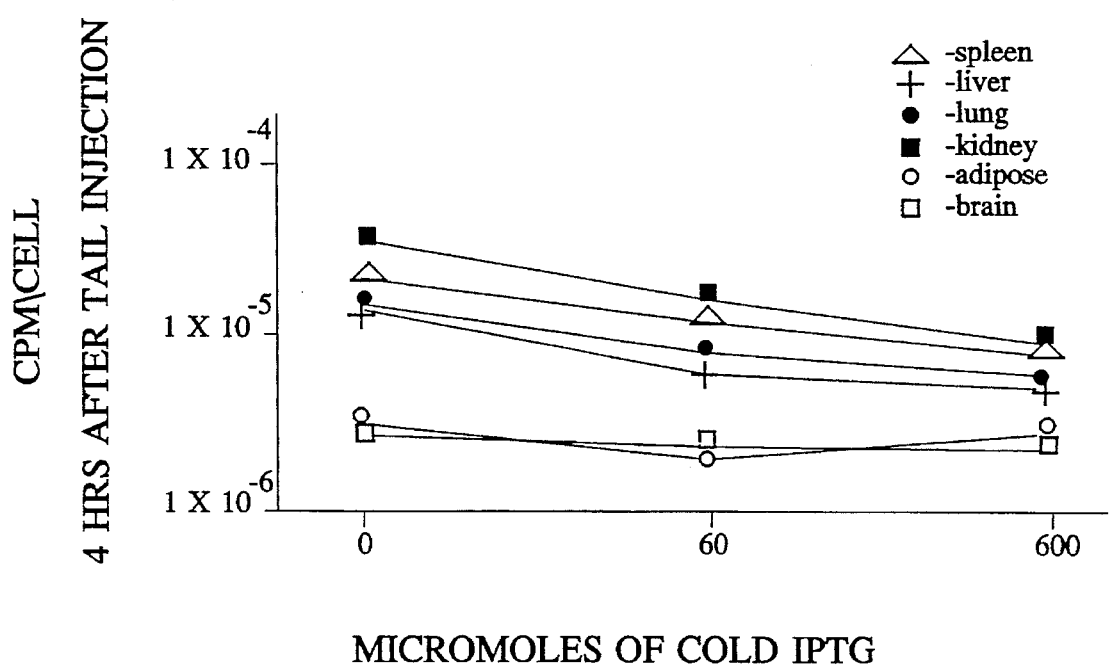

To estimate the maximum level of inducer which can be incorporated into animal cells, tracer amounts of labeled IPTG and MTG were injected into mice with increasing concentrations of unlabeled compound. IPTG and MTG results are shown respectively in FIG. 4A and 4B. For the concentrations tested, 60 and 600 umol of unlabeled compound, no decrease in the level of tracer IPTG was observed in any of the tissues. A slight decrease with MTG was observed. Tissue cells, therefore, exhibited a large capacity for inducer uptake. These results mimic those obtained in cultured cells with little decrease in uptake of labeled compound with the addition of increasing levels of cold inducer.

At the highest concentration of 600 umol, the inducer concentration in the blood reached 300 mM. If this concentration were maintained for extended periods of time, cells would likely die from toxicity. Blood levels, however, were reduced by kidney filtration allowing the cells to survive the initial high doses used for maximal inducer uptake into tissues.

The rate of clearance of the labeled inducers from the blood was measured over a 24 hour period after injection with or without 600 umol of cold compound. Following injection of approximately 200 nmol of inducer, the half life of IPTG in the blood was 20 minutes and was 15 minutes for MTG. With the addition of cold compound, the half-life decreased to 30 minutes for IPTG and 20 minutes for MTG. The effect of adding cold inducer only slightly reduced the clearance kinetics. Therefore, since the half-life of inducer was not decreased significantly with increasing inducer concentrations, blood levels and, consequently, tissue levels can be maintained at the increased levels in a manner that is proportional to the initial blood concentrations.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A nucleic acid construct comprising a DNA sequence encoding a nuclear transport signal peptide operatively linked to a DNA sequence encoding an inducible repressor, where the nuclear transport signal peptide is from an SV40 large T antigen and the inducible repressor is a lac inducible repressor protein, and wherein said DNA sequences are operatively linked to a promoter.

2. A nucleic acid construct which is pPy5' SS1A or pPy(SL)SS1A.

* * * * *